(12) United States Patent
Migneco et al.

(10) Patent No.: US 8,236,350 B2
(45) Date of Patent: Aug. 7, 2012

(54) POLYMER FOR TISSUE ENGINEERING APPLICATIONS AND DRUG DELIVERY

(75) Inventors: Francesco Migneco, Ypsilanti, MI (US); Yen Chih Huang, Ann Arbor, MI (US); Ravi K. Birla, Ann Arbor, MI (US); Scott J. Hollister, Saline, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 282 days.

(21) Appl. No.: 12/533,368

(22) Filed: Jul. 31, 2009

(65) Prior Publication Data

US 2010/0196322 A1 Aug. 5, 2010

Related U.S. Application Data

(60) Provisional application No. 61/137,807, filed on Aug. 1, 2008.

(51) Int. Cl.
*A61F 2/00* (2006.01)
(52) U.S. Cl. ......... 424/484; 424/486; 424/422; 424/423
(58) Field of Classification Search .................. 424/484, 424/486, 422, 423
See application file for complete search history.

(56) References Cited

U.S. PATENT DOCUMENTS

| | | | | |
|---|---|---|---|---|
| 6,017,566 | A * | 1/2000 | Bunczek et al. | .................. 426/3 |
| 6,630,155 | B1 | 10/2003 | Chandrashekar et al. | |
| 6,777,002 | B1 | 8/2004 | Vuaridel et al. | |
| 7,371,400 | B2 | 5/2008 | Borenstein et al. | |
| 2004/0254639 | A1 | 12/2004 | Li et al. | |
| 2006/0154195 | A1 | 7/2006 | Mather et al. | |

OTHER PUBLICATIONS

Wang et al., A tough biodegradable elastomer Nature Biotechnology 20, 602-606 (2002).*
Webb et al., Biodegradable polyester elastomers in tissue engineering Cell and Tissue Based Therapy Jun. 2004, vol. 4, No. 6 , pp. 801-812.*
ASTM D412-98a(2002)e1, "Standard Test Methods for Vulcanized Rubber and Thermoplastic Elastomers—Tension," ASTM International (Jan. 2003).
Dunn, Courtney A. et al., "BMP Gene Delivery for Alveolar Bone Engineering at Dental Implant Defects," Molecular Therapy, vol. 11., No. 2, pp. 294-299 (Feb. 2005) (published online Nov. 6, 2004).
Edwards, P.C. et al., "Sonic hedgehog gene-enhanced tissue engineering for bone regeneration," Gene Therapy, vol. 12, pp. 75-86 (2005) (published online Oct. 28, 2004).
Gunatillake, Pathiraja A. et al., "Biodegradable Synthetic Polymers for Tissue Engineering," European Cells and Materials, vol. 5, pp. 1-16 (2003).
Middleton, John C. et al., "Synthetic Biodegradable Polymers as Medical Devices," Medical Plastics and Biomaterials Magazine, Mar./Apr. 1998, pp. 30-39 (Mar. 1998) (downloaded on Mar. 1, 2012).
Muggli, Dina Svaldi et al., "Reaction Behavior of Biodegradable, Photo-Cross-Linkable Polyanhydrides," Macromolecules, vol. 31, pp. 4120-4125 (1998) (published online May 25, 1998).
Wu, Linbo et al., "In vitro degradation of three-dimensional porous poly(D,L-lactide-co-glycolide) scaffolds for tissue engineering," Biomaterials, vol. 25, pp. 5821-5830 (2004).
Barrett, Devin G. et al., "Thermosets synthesized by thermal polyesterification for tissue engineering applications," Soft Matter, vol. 6, pp. 5026-5036 (2010) (published online Aug. 19, 2010) (downloaded on Jun. 4, 2011).
Migneco, Francesco et al., "Poly(glycerol-dodecanoate), a biodegradable polyester for medical devices and tissue engineering scaffolds," Biomaterials, vol. 30, pp. 6479-6484 (Nov. 2009) (published online Aug. 27, 2009).

* cited by examiner

*Primary Examiner* — Maria Leavitt
(74) *Attorney, Agent, or Firm* — Harness, Dickey & Pierce, P.L.C.

(57) ABSTRACT

A biocompatible and biodegradable elastomeric polymer material, the polymer material comprising: glycerol and dodecanedioic acid, wherein the molar ratio of glycerol to dodecanedioic acid is from about 5:1 to about 1:5. Methods for using the biocompatible and biodegradable elastomeric polymer material comprises providing an PGD elastomeric polymer comprising glycerol and dodecanedioic acid, in a molar ratio of glycerol to dodecanedioic acid of about 1:1 and administering the PGD elastomeric polymer to a soft tissue defect site in needs thereof.

14 Claims, 9 Drawing Sheets

12-(2,3-dihydroxypropoxy)-12-oxododecanoic acid

POLYMER FOR TISSUE ENGINEERING APPLICATIONS AND DRUG DELIVERY

CROSS-REFERENCE TO RELATED APPLICATIONS

This application claims the benefit of U.S. Provisional Application No. 61/137,807, filed on Aug. 1, 2008. The disclosure of the above application is incorporated herein by reference.

FIELD

The present disclosure relates to tissue engineering polymers that are biodegradable and biocompatible for the repair of soft tissue defects.

BACKGROUND

The statements in this section merely provide background information related to the present disclosure and may not constitute prior art.

Degradable biopolymers are a key element in soft tissue engineering. Many elastomers employed for tissue engineering applications are so soft and pliable at room temperature that their surgical implantation can be extremely difficult.

Such elastomeric polymers should exhibit a wide range of properties to address the multitude of needs in soft tissue reconstruction. It is desirable that such polymers mimic soft tissue elasticity, imparting favorable stresses on surrounding tissues, while at the same time withstanding physiologic stresses without failure. Large differentials between normal tissue stresses and device-induced stresses are associated with adverse physiologic responses, such as restenosis in blood vessel grafts.

Furthermore, polymer devices must withstand manipulation during surgical implantation. Specifically, it would be beneficial for the device to maintain a rigid shape during implantation at room temperature, allowing the surgeon to manipulate and insert the devices in the proper anatomical position, subsequently becoming soft and compliant at body temperature to better match soft tissue elasticity. Many of the above described advantages are not presently found in elastomeric polymer compositions commercially available for tissue engineering applications.

SUMMARY

A biodegradable elastomeric polymer composition is provided the elastomeric polymer material includes: a cross-linked polyester having shape memory, the cross-linked polyester having a polymeric unit of monomers of glycerol and monomers of dodecanedioic acid. The molar ratio of glycerol to dodecanedioic acid in the biodegradable elastomeric polymer composition ranges from about 5:1 to about 1:5, preferably 1:1.

Methods for forming a tissue engineered device is also provided in another aspect. The method comprising the steps of: providing a biodegradable elastomeric prepolymer composition, the elastomeric prepolymer composition including a polyester having repeating units of poly(glycerol dodecanoate); placing the prepolymer composition in a device mold having a desired shape; heating the device mold containing the prepolymer at a temperature ranging from about 70° C. to about 500° C., the prepolymer being maintained at a pressure ranging from 760 Torr to about 50 mTorrs thereby thermally curing the prepolymer composition and forming a molded poly(glycerol dodecanoate) device; cooling the molded poly(glycerol dodecanoate) device; and removing the molded poly(glycerol dodecanoate) device from the device mold thereby forming a tissue engineered device.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 4A:
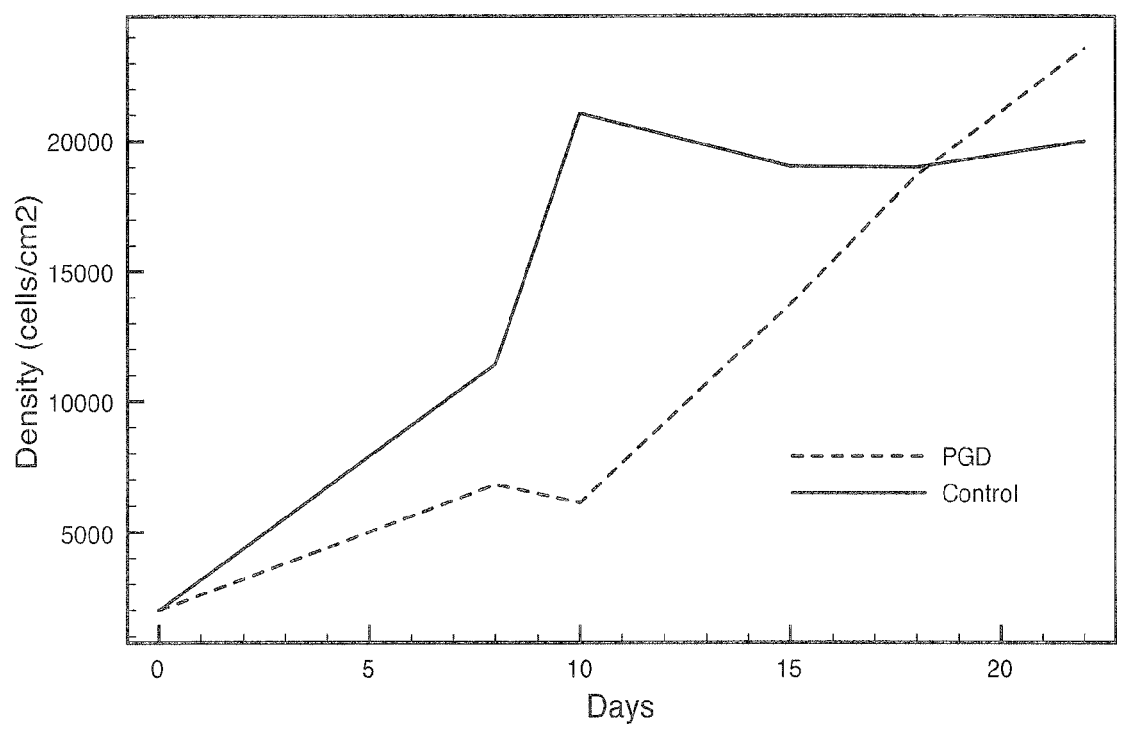
FIG. 4A is a graphical plot of cell density over time. Control cells grown on traditional plastic substrates have a faster growth rate than cells grown on PGD substrates, but eventually, cells growing on PGD plates increase their growth rate reaching the same density around day 18.
Figure 4B:
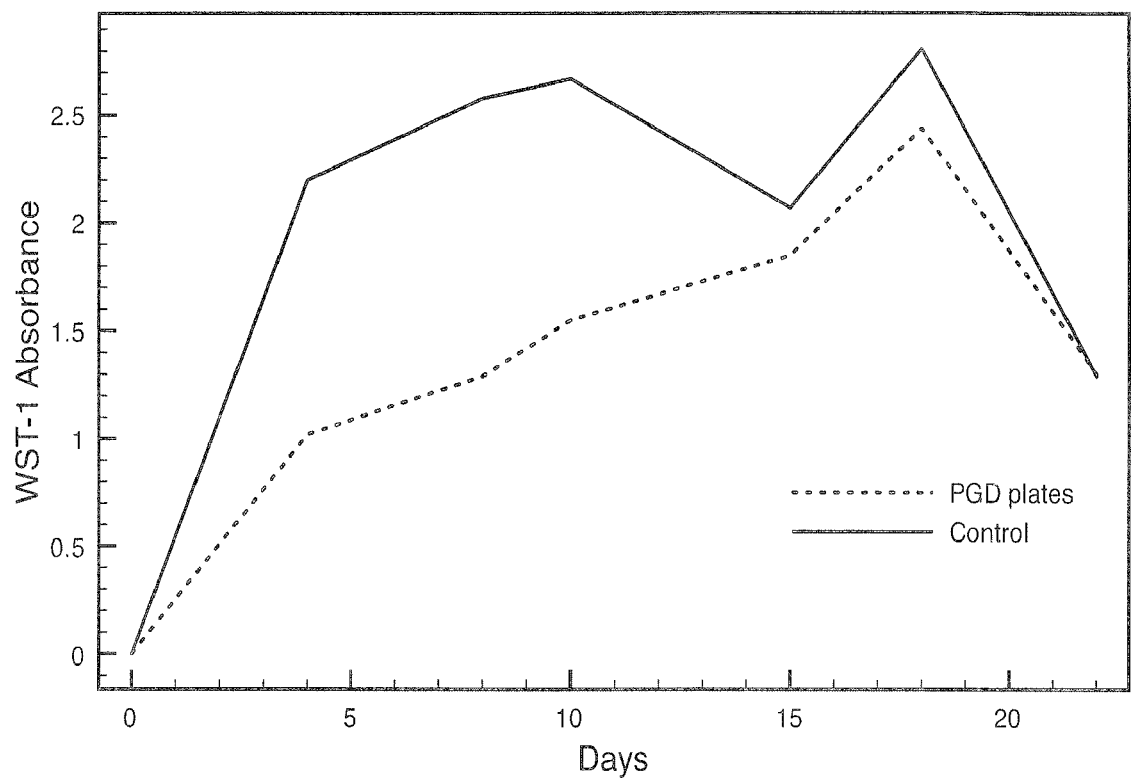

FIG. 4B is a graphical plot of cell proliferation as measured using the WST-1 cell proliferation assay. WST-1 cell proliferation assay shows that fibroblasts remain viable for the duration of the study, in the PGD and control groups. The cell proliferation curves are following a similar pattern of the growth.

Figure 5A:
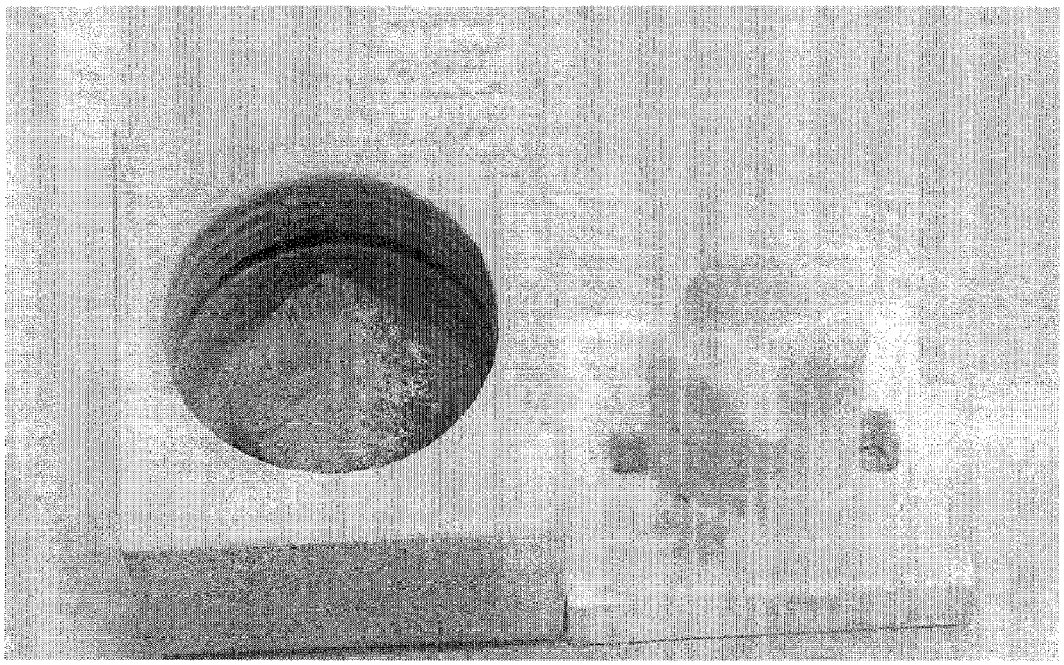

FIG. 5A depicts a photograph of a trileaflet cardiac valve formed using rapid prototyping technique and indirect casting. A wax mold is made by encasing the medical device in wax.

Figure 5B:
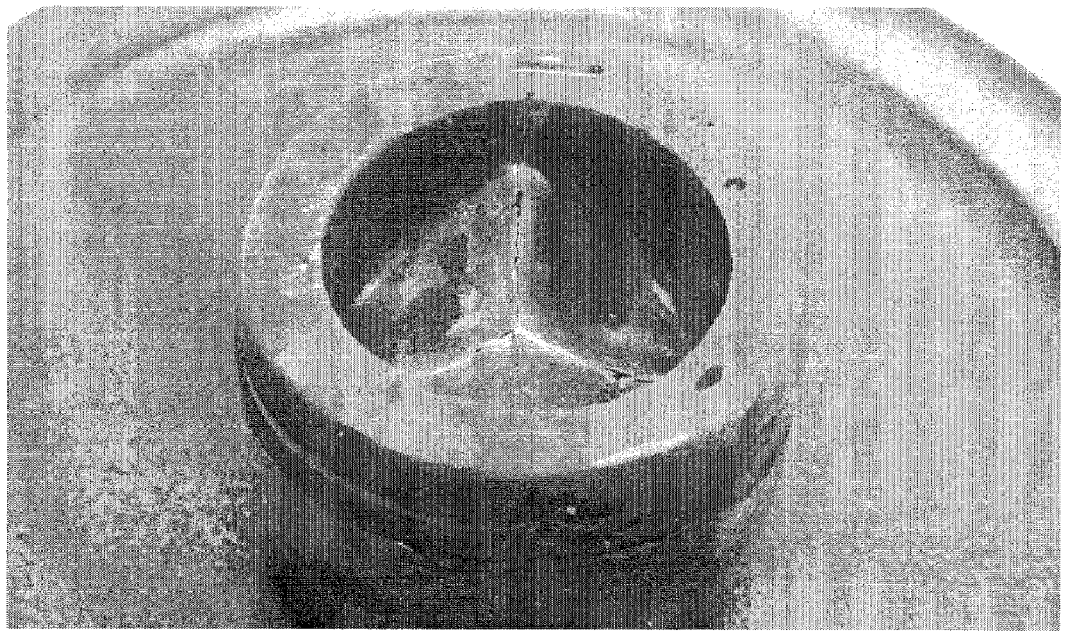

FIG. 5B depicts a photograph of a trileaflet cardiac valve polyurethane replica of the medical device.

Figure 5C:
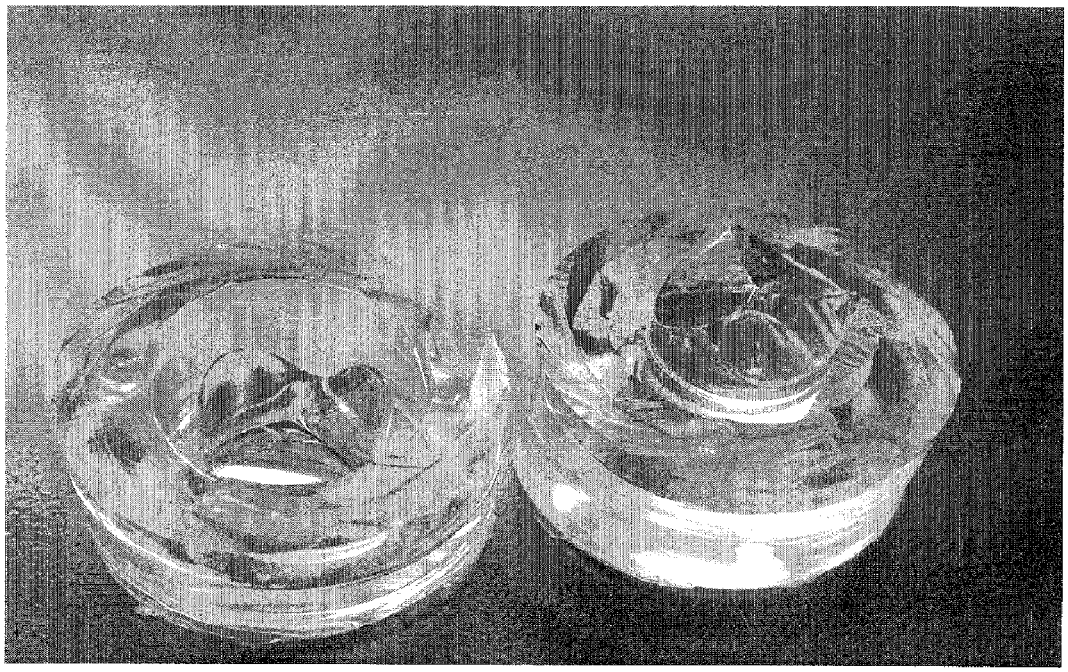

FIG. 5C depicts a photograph of a polydimethylsiloxane intermediate mold obtained using the polyurethane replica as shown in FIG. 5B.

Figure 5D:
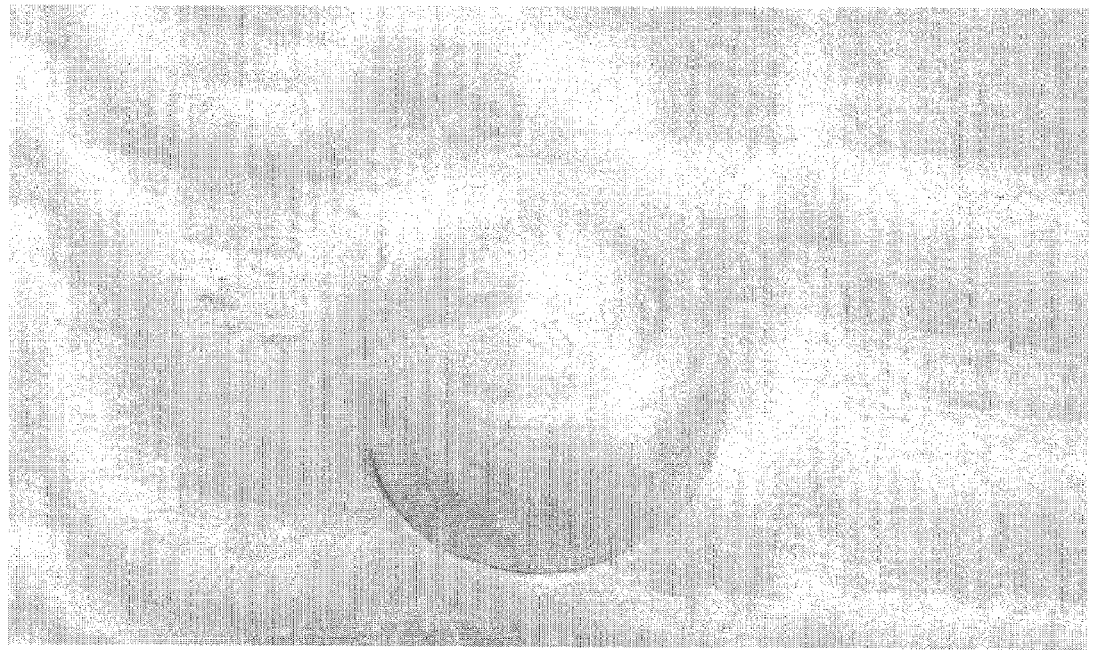

FIG. 5D depicts a photograph of a medical device comprising poly(glycerol dodecanoate) (PGD) elastomeric polymer in accordance with the methods of the present technology.

DETAILED DESCRIPTION

The following description is merely exemplary in nature and is not intended to limit the present disclosure, application, or uses.

The present technology provides polymer materials formed from the condensation polymerization of glycerol and 1,12, dodecanedioic acid to form the elastomeric polymer: poly(glycerol dodecanoate) or the IUPAC name 12-(2,3-dihydroxypropoxy)-12-oxododecanoic acid, a biocompatible and biodegradable polymer suitable for tissue engineering applications. The present elastomeric materials have been found to exhibit excellent biodegradability and biocompatibility properties. The elastomeric composition of the present technology can be modified to provide engineered replacements for cartilage and other soft tissue material having desired strain at break and modulus values that enable the soft tissue replacement to have preselected mechanical features.

PGD shows a unique property, namely, in the cured status, modulus and strain at break can be modulated by varying the external temperature. PGD has a long degradation time and shows good in-vitro biocompatibility. PGD is believed to impart features which are suitable for fabricating soft tissue engineered devices.

Poly Glycerol Dodecanoate (PGD) Elastomeric Materials

Figure 1:
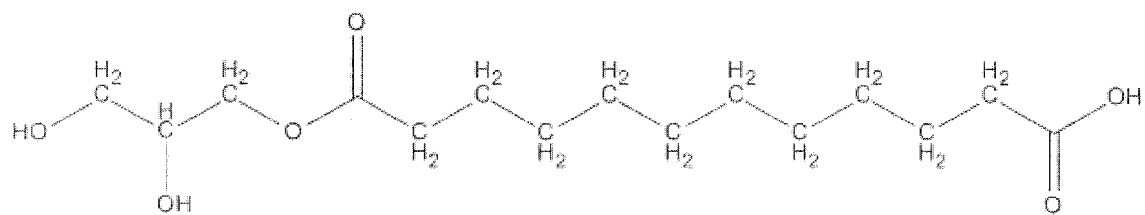
FIG. 1 is a chemical structure of poly(glycerol dodecanoate) (PGD).

PGD elastomeric polymers for use as biodegradable and biocompatible polymer materials for tissue engineering and drug delivery devices can be formed by the condensation reaction between glycerol and an organic dicarboxylic acid, for example, a fatty acid. In some embodiments, the fatty acid can include dodecanedioic acid. These two components can be mixed in a 1:1 ratio to form the present elastomeric materials. The PGD elastomeric polymer is illustratively shown in FIG. 1. Reaction between glycerol and dodecanedioic acid in a 1:1 molar ratio yields an elastomer that is soft and pliable out of the oven, hardening upon cooling at room temperature. Elemental composition of the repetitive unit is: (calculated for $C_{15}H_{28}O_6$) C=59.19%, H=9.27%, O 31.54%. Its calculated average mass is 304.37 Da. Without wishing to be limited to any particular theory, it is believed that the formation of a PGD elastomeric polymer occurs by polycondensation of glycerol and dodecanedioic acid.

Figure 2A:
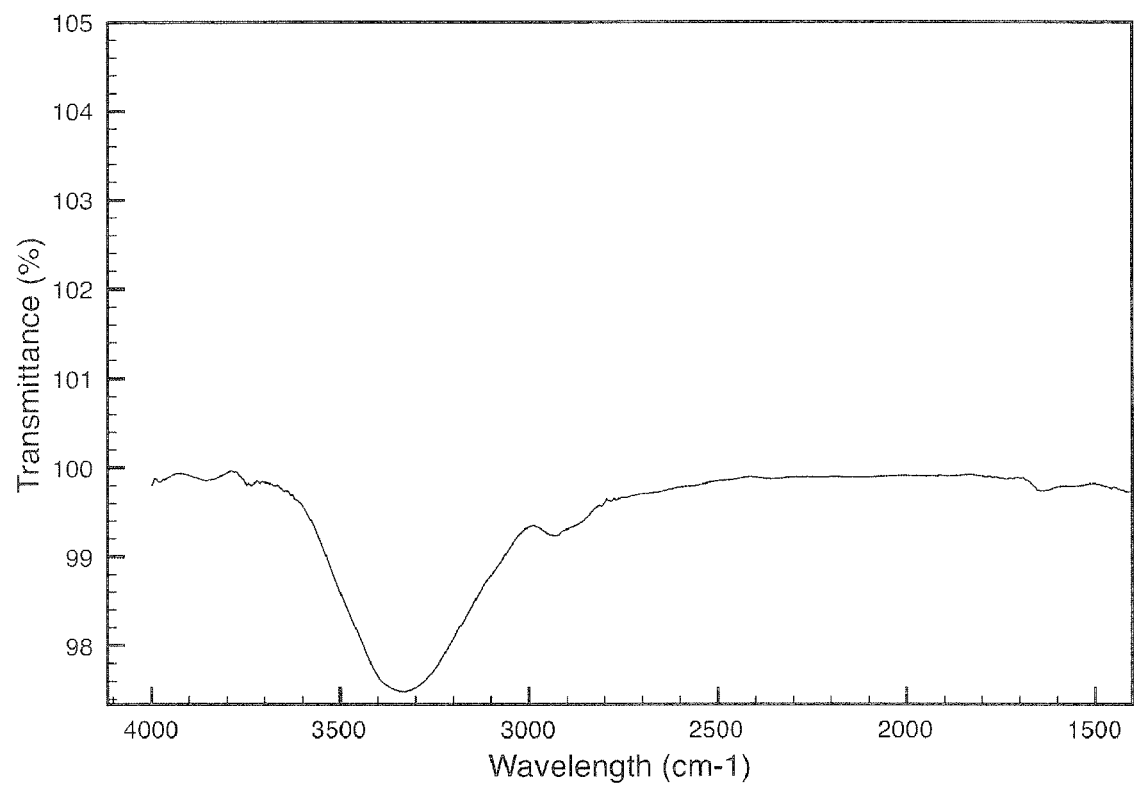
FIG. 2A depicts a Fourier Transformed Infra-Red (FTIR) spectra of uncured PGD. As shown in the spectra, a broad peak is visible at 3331 $cm^{-1}$ and denotes the presence of alcohol-associated hydroxyl groups.
Figure 2B:
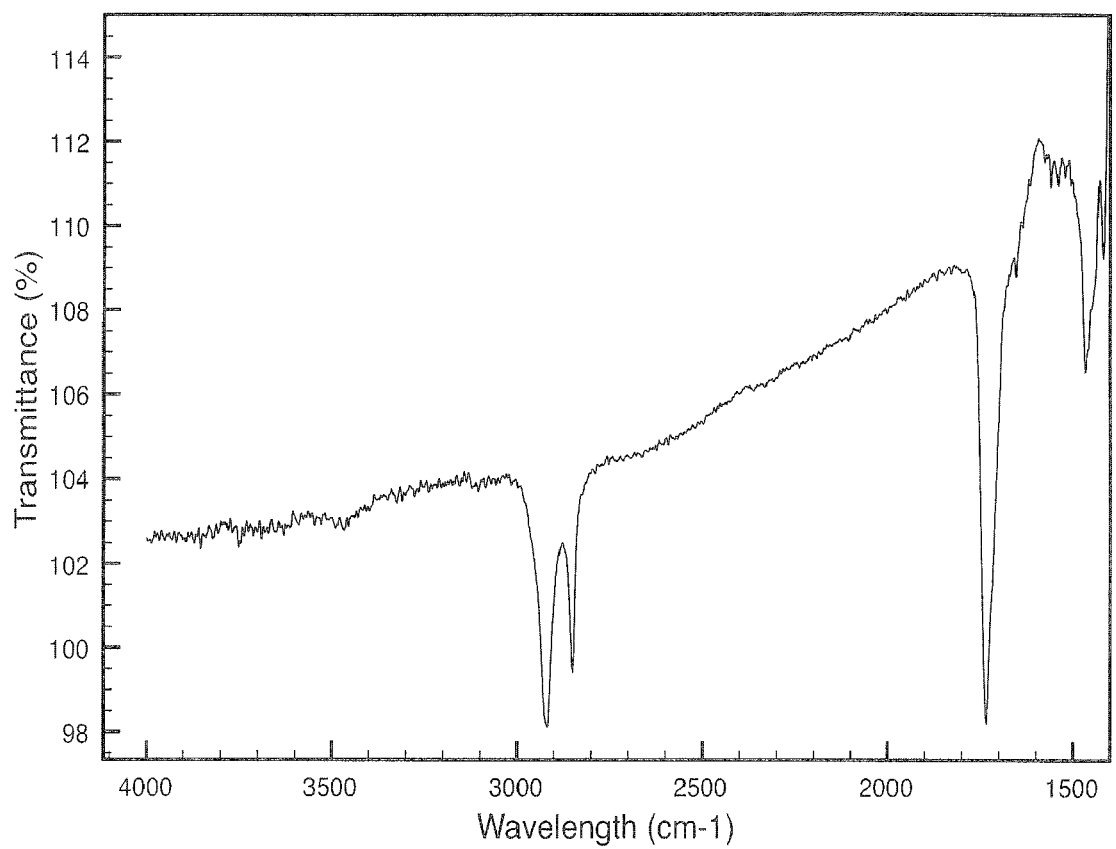
FIG. 2B depicts a Fourier Transformed Infra-Red (FTIR) spectra of cured PGD. The spectra of the cured PGD indicates the OH peak at 3331 $cm^{-1}$ has disappeared and a C=O stretch at 1735 $cm^{-1}$, typical of esteric bond appears.

Fourier Transformed Infra-Red (FTIR) analysis on pre-polymer slabs confirmed a broad OH stretch, at 3331 $cm^{-1}$, partially masking a methyl stretch at 2927 $cm^{-1}$ (FIG. 2A). On fully cured slabs the O—H stretch at 3331 $cm^{-1}$ is absent unmasking the methyl stretch at 2927 $cm^{-1}$, and an intense C=O stretch, indicative of esteric bonds, appears at 1735 $cm^{-1}$ (FIG. 2B). Thermogravimetric analysis (TGA) of the present PGD elastomeric polymer shows no melting point in the range from 25° C. to 900° C., with PGD elastomeric polymer undergoing a complete combustion at about 700° C. In some embodiments, the glass transition temperature ($T_g$) of the present PGD elastomeric polymers range from about 31° C. to about 35° C., more preferably from about 31° C. to about 34.2° C. and has an average $T_g$ of about 32.1° C. using differential scanning calorimetry.

In some embodiments, the mechanical properties of the PGD elastomeric polymers differ significantly upon the temperature of the material at use or testing. Thus, during extension at 21° C., PGD elastomeric polymers exhibit a typical linear elastic stress strain response followed by necking and plastic deformation of an elastic-plastic material, while at 37° C. PGD elastomeric polymers exhibit a non-linear elastomeric response (See FIGS. 3(A) and 3(B)). As used herein, the tensile tests reported on cured specimens were performed in compliance with the ASTM International, American Society for Testing and Materials (ASTM) D412-98a standard. Strain at break (SAB), and modulus acquired at four different ambient temperatures (25° C., 34° C., 37° C., 42° C.) (n=20). In some embodiments, the tangent Young modulus dropped from a maximum ranging from (67.2-155.7, average 136.55) MPa. to (0.25-2.6, average 1.08) MPa at 21° C. and 37° C. respectively. The tangent modulus of the PGD elastomeric polymers at 37° C. can be calculated at a strain level of 7.8% (5.5-9.8). Strain at break (SAB) at 21° C. can range from about 192.1% to about 243.5% (average 225%) dropping to about 62.9% to about 163.6% (average 123.2%) at 37° C. (Tab. 1)

In some embodiments, the PGD elastomeric polymers can have one-term Ogden constants of about $\mu_1$=0.3±0.12 MPa, $\alpha_1$=2.14±0.5 with $R^2$=0.998±0.001 for the nonlinear elastic response at 37° C. The present PGD elastomeric polymers can be modeled using classic hyper-elastic models. In some embodiments, the PGD elastomeric polymers of the present technology exhibit excellent hydration and biodegradability properties suited for in vivo implantation. For example, normalized change in dry weight of the PGD elastomeric polymer was negligible in the first 20 days of soaking in PBS at 37° C., at 40 days. The weight of the PGD elastomeric polymer dropped to an average of 94.2% (ranging from about 93% to about 96%), progressing to an average of about 87.4% (ranging from about 85 to about 89%) at 90 days. Fitting a linear regression model to the data obtained, the rate of degradation of the present PGD elastomeric polymer can be modeled by the function y=−0.001x+1 where y is the ratio of residual biopolymer, −0.001 is the rate of degradation, x is the time in days and the coefficient 1 is the amount of polymer at time 0. This function provides that the PGD elastomeric polymer of the present technology has an in-vivo degradation behavior with a p-value less than 0.005%, and an $R^2$ of 0.978. This formula can be used to calculate the time at which the present PGD elastomeric polymers would be reduced to 50% of its original weight (half-life). In some embodiments, the half-life of the present PGD materials ranges from about 12 months to about 24 months, or from about 14 months to about 20 months, or from about 15 months to about 18 months and still more preferably from about 15 months to about 17 months. In some embodiments, the time at which the present PGD elastomeric polymers would be reduced to 50% of its original weight (half-life) is about 16 months when implanted in vivo or in a physiological buffer.

It is to be understood that in the formation of a polymer network that the links and polymer strands of the network are not homogeneous. In various aspects of the present invention, the formation of different cross-links in the polymer network is exploited to adjust, or even "tailor" the properties of the resultant polymer. PGD elastomeric polymer composition can include a polyester of glycerol and dodecanedioic acid, with esteric bonds between the glycerol OH groups and the dodecanedioic acid carboxylic groups. Upon FTIR analysis, the PGD elastomeric polymer shows the presence of a broad stretch at 3331 $cm^{-1}$ in the pre-polymer phase, indicating the predominance of alcohol-associated OH and therefore a rather un-reacted compound. The same peak is absent in the fully cured polymer where an intense C=O stretch, typical of esters, appears at 1735 $cm^{-1}$. The length of dodecanedioic acid and the number of esteric bonds it forms with glycerol are responsible for the unique thermomechanical characteristics of PGD.

At 21° C. strain at break was more than three times its original length, and more than twice its initial length at 37° C. The modulus also changed significantly, indicating a stiff material at room temperature, which became soft and pliable at body temperature. Therefore, PGD shows the typical features of a stiff elastic-plastic material at room temperature (with a very high elongation at break and high modulus), and the properties of a nonlinear elastomer at body temperature. In some embodiments, the PGD elastomeric polymer can have a similar or identical cross-linking density and mechanical characteristics of styrene-butadiene rubber (synthetic rubber) when heated to 37° C.

It is believed that the dual behavior of the PGD elastomeric polymer of the present technology can be accounted for by the PGD elastomeric polymer $T_g$. At room temperature, the PGD elastomeric polymer backbone possess only molecular vibrational motion, and no other molecular motions are present; the polymer is in fact "frozen" in its hard and glassy state. As the temperature increases, approaching $T_g$ (32° C.), the backbone acquires rotational motion along its major axis, and as the temperature increases further, the secondary interactions between adjacent polymer chains become looser and looser and now contiguous chains are free to move with one respect to another. Since we did not observe any change in the mechanical properties from 37° C. and 42° C., we conclude that at 37° C. the polymer has lost its "glassy" state and is completely amorphous. This data is also confirmed by DSC showing the "step-wise" anomaly that describes the glass transition, ending at about 35° C.

The immediate clinical implication of this unique behavior is clear during implantation, especially for soft tissues, in which the main difficulty encountered is to re-establish the correct 3D shape of a soft implant and even more importantly re-establish the normal anatomical relationship with the surrounding host structures. Implants fabricated from PGD, being stiff and maintaining their 3D shape at room temperature, would be easier to manipulate and to place in the correct anatomical position.

In some embodiments, the PGD elastomeric polymer tensile data at 37° C. can be fit to a one-term Ogden model, which is a classical model describing behavior of hyper-elastic materials. In some embodiments, the PGD elastomeric polymer compositions described herein can be explained by a valid model used to predict the mechanical behavior of biomedical devices, drug delivery constructs and tissue engineered materials fabricated with PGD elastomeric polymer compositions of the present technology using commercially available finite element codes. To obtain different PGD elastomeric materials having tailored mechanical properties suitable for different biomedical device fabrication and tissue engineered materials, one can exploit and estimate and predict how the material behaves, and therefore, select the design, and material composition more suitable for the desired purpose.

Shape memory can generally be characterized by a peculiar thermo-mechanical response to heat, defining three temperature states: 1) Deformation temperature (Td) is the temperature at which the polymer can be deformed into its temporary shape and it can be higher or lower than the $T_g$; 2) Storage temperature is the temperature below which no recovery from the deformed state occurs, it can be lower or the same of the Td; and 3) Recovery temperature (Tr) is the temperature at which the memory effect is active and the polymer returns to its original shape, and this temperature is typically around $T_g$.

PGD elastomeric polymers of the present technology possess essentially two temperatures ranges: temperature of cold deformation ($Td_c$) and temperature of warm deformation ($Td_w$). $Td_c$, below the glass transition temperature, is the temperature at which the polymer is in its glassy state, where cold draw and plastic deformation are possible. In this range of temperatures the deformation is maintained even after the external forces are removed. $Td_w$, few degrees higher than the $T_g$, (~37° C.) is the temperature at which the PGD elastomeric polymer has completed its transition to a rubber-like state as characterized by a non-linear elastic deformation of the polymer. The deformation may not be maintained once the external forces are removed, unless the deformed system is cooled down below the $T_g$. In some embodiments, the PGD elastomeric polymer of the present technology, when in a deformed configuration starts recovering its original shape if heated up to the $T_g$, and the recovery rate becomes faster as the temperature increases, with an optimal recovery temperature around 39-40° C.

$Td_c$ and $Td_w$ have an important macroscopic significance for the PGD elastomeric polymers described herein, namely that: 1) PGD elastomeric polymer can undergo large plastic deformation by cold extension, and when heated to 32° C. and higher returns to its initial configuration, this process is faster as the temperature increases; and 2) PGD can be deformed while in its rubbery state, and maintain the deformed configuration if cooled below glass transition temperature.

In some embodiments, a biodegradable PGD elastomeric material formed from the a composition of the present invention not containing a different polymer or co-polymer, is provided that has one or more of the following properties: (a) a tensile Young's modulus less than about 1.5 MPa when measured according to ASTM standard D412-98a; (b) a tensile Young's modulus greater than about 0.05 MPa and an elongation of greater than about 45%, both when measured according to ASTM standard D412-98a; (c) a Young's modulus in the range between about 0.4 MPa and about 0.55 MPa when measured according to ASTM standard D412-98a; (d) a maximum elongation greater than about 170%;

Biocompatibility

As used herein, "biodegradable" polymers can include polymers that degrade down to monomeric species under physiological or endosomal conditions. In some embodiments, the PGD elastomeric polymers and polymer biodegradation byproducts are biocompatible. Biodegradable PGD elastomeric polymers are not necessarily hydrolytically degradable and may require enzymatic action to fully degrade. The term "biocompatible", as used herein is intended to describe materials that do not elicit a substantial detrimental response in vivo. In-vitro biocompatibility can be assessed by seeding ovine artery fibroblasts on Petri dishes, coated with 1% PGD elastomeric polymer and observed under microscope daily for two weeks.

PGD is a polymer derived from condensation of glycerol and dodecanedioic acid, and is safe for human use. Its varying mechanical features together with its biocompatibility make it a good candidate for soft tissue engineering, allowing an ease of manipulation and implantation when in its plastic state, and becoming readily soft and pliable upon implantation in the body.

Degradable biopolymers are a key element in soft tissue engineering. Many elastomers employed are so soft and pliable at room temperature that their surgical implantation can be extremely difficult. PGD shows unique properties, including, for example, when in the cured status, the modulus and strain at break of the PGD elastomeric polymers can be modulated by varying the external temperature. This material has a long degradation time and shows good in vitro biocompatibility. Without wishing to be bound by any particular theory, it is believed that PGD elastomeric polymer features are suitable for fabricating soft tissue engineered devices.

Poly Glycerol Dodecanoate (PGD) Composite Materials

In some embodiments, the PGD elastomeric polymer is admixed with, coated on and/or attached to a second compound or molecule forming a PGD composite material. In some embodiments, a PGD composite material can include a second biocompatible and/or biodegradable material, an organic molecule, an inorganic molecule, a biologically active agent either in solution or in an encapsulated form and combinations thereof. In some embodiments, a PGD elastomeric polymer can be admixed with one or more optional materials to form composites for tissue engineering applications. For example, the PGD elastomeric polymer material can be admixed with one or more of particles (including one or more of granules, powders, chips and shavings), or solutions of calcium phosphate, hydroxyapatite, calcium sulfate, calcium carbonate and mixtures thereof or other ceramics, bioactive glass particles and the like which can be embedded within a PGD elastomeric polymer material to create a PGD ceramic composite.

In some embodiments, the PGD elastomeric polymer can be admixed with one or more porogen materials, for example, porogen particles, thereby forming a PGD composite material that will become porous. In some embodiments according to the present technology, the PGD composite material can include porogen particles embedded within the bulk PGD polymer material and/or on its surface. In some embodiments of a porogen particle-containing PGD composite material, the composition can contain about 50% to about 90% by volume porogen particles. In some embodiments, the PGD composite material can comprise about 55% or more by volume porogen particles, or about 60% or more, about 65% or more, about 70% or more, about 75% or more, about 80% or more, or about 85% or more by volume porogen particles. In some embodiments, the composition can contain about 90% or less by volume porogen particles. In some embodiments, the composition can contain about 75% to about 90% porogen particles.

In some embodiments, the composition can contain 80% or more by volume porogen particles, or more than 80%, or about 81% or more, or 81% or more, or more than 81%, or about 82% or more, or 82% or more, or more than 82%, or about 83% or more, or 83% or more, or more than 83%, or about 84% or more, or 84% or more, or more than 84%, or 85% or more or more than 85%. In some embodiments, the composition can contain from 80% to about 90% by volume porogen particles, or from more than 80% to about 90% porogen particles. In some embodiments, the composition can contain from about 85% to about 90% porogen particles.

Porogen particles useful herein can be made of any biocompatible, biodegradable substance that can be formed into a particle capable of at least substantially retaining its shape during processing of the PGD composite material and until subjected to biodegradation-type conditions, e.g., in vivo conditions. Such substances can also be referred to herein as porogen particle materials or porogen particle "wall" materials.

The biocompatible, biodegradable substance(s) for the porogen particles can be inorganic or organic. In some embodiments, the biocompatible, biodegradable substance selected can be an organic polymer, such as a synthetic organic polymer, e.g., poly(vinyl alcohol), or a combination thereof with another polymer or a bioactive substance. Alternatively, or in addition, the organic, biocompatible, biodegradable substance can comprise demineralized bone matrix, and/or a mono-, di-, or poly-saccharide. In some embodiments, the biocompatible, biodegradable substance selected can be: a calcium salt or compound; sodium chloride; or a mixture thereof; or a calcium phosphate or mixture thereof; or a combination of any of the foregoing comprising a bioactive substance.

In some embodiments, the porogen particles can have a morphology that is any one or more of at least substantially cylindrical, at least substantially prismatic, at least substantially pyramidal, at least substantially regular polyhedral, at least substantially paraboloidal, at least substantially lenticular, at least substantially ovate, or at least substantially spherical. In some embodiments, the porogen particles can include those that are at least substantially regular polyhedral, at least substantially lenticular, at least substantially ovate, or at least substantially spherical. The porogen particles can be "solid" particles, i.e. non-hollow, non-laminar particles containing the biocompatible, biodegradable substance(s); they can be hollow particles having at least one wall defining an internal "empty" space, i.e. one that is devoid of a wall material, but that can be filled with a different solid or fluid material, e.g., a bioactive substance; or they can be laminar particles having a core and at least one distinct layer, the core and layer(s) thereof being independently any wall material, the layers of the particle not defining an "empty" space, but being positioned adjacent one to the next. Hollow particles include those particles that have both laminar features and hollow space(s).

Porogen particles for use in an embodiment of the present technology can have at least one dimension (i.e. axial, transverse, or lateral dimension) that is about 100 to about 500 microns. In one embodiment, all porogen particles of a given morphology can have at least one average axial, transverse, or lateral dimension that is about 100 to about 500 microns. In some embodiments, all porogen particles used can independently have at least one axial, transverse, or lateral dimension that is about 100 to about 500 microns. In some embodiments, all porogen particles used can collectively have at least one average axial, transverse, or lateral dimension that is about 100 to about 500 microns.

In some embodiments, at least one dimension of the porogen particles can be about 100 microns or more, or about 120 microns or more, or about 140 microns or more. In some embodiments, at least one dimension of the porogen particles can be about 500 microns or less, about 425 microns or less, about 350 microns or less, about 300 microns or less, or about 250 microns or less. In some embodiments, the porogen particles can have at least one dimension that is about 120 to about 350 microns. In some embodiments, these gradations also apply to independent, average, and/or collective dimensions as described above. In some embodiments, at least two of the axial, transverse, and lateral dimensions of the particle can independently be about 100 to about 500 microns; in some embodiments, the axial, transverse, and lateral dimensions of the particle can independently be about 100 to about 500 microns.

In some embodiments, the porogen particles can have a ratio of average width (lateral and transverse dimensions) to average length (main axial dimension) that is about 5:1 to about 1:5, or about 4:1 to about 1:4, about 3:1 to about 1:3, about 2:1 to about 1:2; in some embodiments, the porogen particles can have a ratio of average width to average length that is about 1:1.

In some embodiments, the porogen particles used in the bone graft material can have at least about the same morphology. In some embodiments, the porogen particles used in the bone graft material can have at least about the same morphology and at least about the same size.

Polymers for Porogen Particles

In some embodiments of a porogen particle-containing PGD composite material, the particles can comprise a biodegradable, biocompatible polymer. For purposes of the present technology, a biodegradable polymer is considered a biocompatible polymer if it is not unduly immunogenic (according to a reasonable risk-benefit analysis in sound medical judgment), and does not biodegrade to form undesirable insoluble deposits or toxic byproducts that cannot be further catabolized in vivo to form non-toxic products. Similar definitions apply for other biodegradable, biocompatible substances useful herein.

Common classes of biodegradable, biocompatible polymers useful herein include: polyesters, including polyhydroxyalkanoates, polylactones (e.g., polycaprolactones), and poly(propylene fumarates); polyanhydrides, e.g., poly(sebacic anhydride); tyrosine-derived polycarbonates (see, e.g., Muggli et al., *Macromolecules* 31:4120-25 (1998)); polyorthoesters; copolymers of any one or more of these with one another and/or with other biocompatible polymerizable units; and the biodegradable, biocompatible polymers described in U.S. Pat. No. 6,630,155 to Chandrashekar et al. and U.S. Pat. No. 6,777,002 to Vuaridel et al.; and US Patent Publication No. 2004/0254639 to Li et al.

The monomers from which the biocompatible, biodegradable polymers useful herein are made can be $C_1$-$C_{18}$ monomers, such as: $C_2$-$C_{12}$, $C_2$-$C_{10}$, $C_2$-$C_8$, $C_2$-$C_6$, or $C_2$-$C_4$ monomers. The polymers hereof can be homopolymers or heteropolymers of any conformation, e.g., linear, branched (including hyperbranched), cross-linked, or cyclic, etc. Useful copolymers can be statistical, random, alternating, periodic, block, or graft copolymers. By way of example, biodegradable polyhydroxyalkanoate copolymers useful herein can be, e.g., lactide, glycolide, or hydroxybutyrate copolymers synthesized with: other hydroxyacyl monomers, segments, or branches; polyalkylene oxide monomers, segments, or branches; diol or polyol monomers, segments, or branches, such as polyalkylene glycol (e.g., polyethylene or polypropylene glycol) monomers, segments, or branches; carbohydrate (including sugar alcohol, sugar acid, and other sugar derivative) monomers, segments, or branches; amino acyl monomers, segments, or branches; and/or other biocompatible polymerizable units.

Examples of polyhydroxyalkanoate polymers include: poly(lactide) polymers, poly(glycolide) polymers, and poly(hydroxybutyrate) polymers, wherein the monomer units from which these are formed can have any chirality or combination of chiralities; copolymers that represent combinations of these; and copolymers that represent a combination of any of the foregoing with another hydroxyacid monomer or polymerizable monomer of another type. Examples of polyhydroxyalkanoate polyester polymers include poly(glycolide), poly(L-lactide), poly(D,L-lactide), poly(L-lactide-co-glycolide), poly(L-lactide-co-D,L-lactide), poly(D,L-lactide-co-glycolide), poly(3-hydroxybutyrate), poly(3-hydroxybutyrate-co-3-hydroxyvalerate), and poly(glycolide-co-trimethylene carbonate).

The (weight average) molecular weight of biodegradable polymers typically used in bone tissue substitute materials, and which can be used in some embodiments hereof, are, e.g.: about 2,000 or more, about 5,000 or more, about 10,000 or more, about 20,000 or more, about 30,000 or more, about 40,000 or more, or about 50,000 or more MW; about 100,000 or less, about 90,000 or less, about 80,000 or less, about 70,000 or less, about 60,000 or less, or about 55,000 or less MW; and about 2,000 to about 100,000 MW, more typically about 5,000 to about 100,000 MW, about 10,000 to about 90,000 MW, about 20,000 to about 80,000, about 30,000 to about 70,000, or about 40,000 to about 60,000 MW, with about 50,000 to about 55,000 MW being common. Any such molecular weight biocompatible, biodegradable polymer can be used in an embodiment of the present technology, and can be selected in conjunction with other factors that influence porogen particle in vivo degradation rates.

In vivo degradation rates for biocompatible, biodegradable polymers are discussed, e.g., in P A Gunatillake & R. Adhikari, Biodegradable synthetic polymers for tissue engineering, *Eur. Cells & Mater.* 5:1-16 (2003); and J C Middleton & A J Tipton, Synthetic biodegradable polymers as medical devices, *Med. Plastics & Biomater.* March/April 1998: 30-39 (March 1998), both of which are incorporated herein in their entireties. In vitro degradation rates for 10 mm diameter cylindrical samples of polyhydroxyalkanoates are described in L Wu & J Ding, In vitro degradation of three-dimensional porous poly(D,L-lactide-co-glycolide) scaffolds for tissue engineering, *Biomaterials* 25:5821-30 (2004). Based on these data, the following estimated approximate rates of degradation can be typically expected for biodegradable polymers commonly used in PGD composite materials.

TABLE 1

Typical Degradation Rates for Selected Biocompatible, Biodegradable Polymers

| Poly(L)LA | 45 μm/wk |
|---|---|
| Poly(e-caprolactone) | 45 |
| Poly(D,L)LA | 90 |
| PGA | 140 |
| PGA-co-Me$_3$-carbonate | 140 |
| Copoly(D,L)L/GA 85:15 | 260 |
| Poly(propylene-fumarate) | 330 |
| Copoly(D,L)L/GA 75:25 | 520 |
| Copoly(D,L)L/GA 50:50 | 770 |

In Table 1: Poly(L)LA is poly(L-lactic acid); poly(e-caprolactone) is poly(epsilon-caprolactone); poly(D,L)LA is poly(D-,L-lactic acid); PGA is poly(glycolic acid); PGA-co-Me3-carbonate is poly(glycolic acid-co-trimethylene carbonate); copoly(D,L)UGA 85:15, 75:25, and 50:50 are poly(D-,L-lactic acid-co-glycolic acid) polymers respectively having approximate molar proportions of 85:15, 75:25, and 50:50 lactic acid:glycolic acid monomers; and poly(propylene-fumarate) is poly(propylene glycol-co-fumaric acid).

Resorption rates, as used herein, refer to rates of resorption for individual particles that are directly in contact with biological fluid at least in part, e.g., along at least one surface zone thereof. It can be understood that many uses of a PGD composite material for tissue engineering applications can produce an in vivo mass of PGD composite material in contact with tissue, for example, cartilage, tendons, ligaments, nerves, blood vessels and bone, the mass of PGD composite material containing both porogen particles partly embedded along a surface of the mass, and thus directly exposed to biological fluid, and porogen particles buried within the mass. Those porogen particles that are buried most distally from biological fluid sources may not be resorbed until a point in time later than that at which the original surface-exposed particles will have become resorbed, particularly in the case where the porogen particle material is or includes substance(s), such as calcium salts, bioactive glass, demineralized bone matrix or other biomineralizing organic matrix materials, that are mainly resorbed by action of cells, rather than by contact with fluid alone. However, use of quickly resorbing porogen particles in the PGD composite material, as taught herein, reduces the overall time until resorption of the mass' entire population of particles of a given type is complete.

Although the microns-per-week resorption rates recited in Table 1 can be typical for in vitro degradation of commonly used versions of these polymers (e.g., typically having a 30,000-60,000 MW), a variety of factors can result in different degradation rates. For example, use of a relatively lower molecular weight version of a particular polymer would be expected to increase the overall rate of degradation and dissolution of the polymer in vivo. Alternatively, use of a copolymer formed from that polymer's units with another, more hydrolyzable species, e.g., a hydroxyacid and a biologically hydrolyzable carbohydrate(s) or peptide(s), would be expected to increase the rate of bulk degradation, since hydrolysis of the, e.g., carbohydrate or peptide units enhances fragmentation, resulting in lower molecular weight polymer substrates as an intermediate for degradative dissolution. Other factors and their relative effects on degradation rates for a given polymer are likewise known to one of ordinary skill in the art, e.g., polymer architecture, particle shape (geometry), particle morphology (internal structure, e.g., solid, hollow, laminar, etc.), surface area-to-volume ratio, degree of encapsulation in matrix, pH of the local in vivo environment, and accessibility of in vivo fluids and/or cells to the polymer. These factors can be used to calculate a specific formulation of PGD composite material having appropriate quantities and types of resorbable materials for a specific application in vivo.

Porogen Particle Additives

The material chosen for the substance of the porogen particle bulk, wall(s)/layer(s), and/or core structures can be a pure substance, as any of the polymers and copolymers, compounds, and whole (processed) tissues and tissue fragments described above, or it can be a mixture of such substances. Where a mixture is used, it can comprise any combination of the above-described porogen particle materials in any proportions. The mixture can further comprise a minority of any one or more agents that are: processing aids, such as binders (e.g., cellulose ethers) and lubricants (e.g., fatty acids); storage aids, such as preservatives and dryness-promoting agents; rehydration aids, such as wetting-facilitation agents; alginate; and the like. In some embodiments, such agents can constitute less than 20%, or about 15% or less, or about 10% or less, or about 5% or less, or about 4% or less, or about 3% or less, or about 2% or less, or about 1% or less of the mixture. Thus, the material provided for the substance of the porogen particle can be any such compound or mixture.

The porogen particles can further contain one or more added bioactive agent, either: (1) encapsulated in one or more hollow space(s) within a "hollow" particle; or (2) located within or throughout the bulk of a "solid" particle, or of a core, wall, or layer of a hollow or laminar particle. Examples of bioactive agents for use in an embodiment of the present technology include: bone morphogenic proteins (e.g., BMP1-BMP17), bone-derived growth factors (e.g., BDGF-1, BDGF-2), transforming growth factors (e.g., TGF-alpha, TGF-beta), somatomedins (e.g., IGF-1, IGF-2), platelet-derived growth factors (e.g., PGDF-A, PGDF-B), fibroblast growth factors (e.g., αFGF, βFGF), osteoblast stimulating factors (e.g., OSF-1, OSF-2), and sonic hedgehog protein (SHH); other hormones, growth factors, and differentiation factors (e.g., somatotropin, epidermal growth factor, vascular-endothelial growth factor; osteopontin, bone sialoprotein, α2HS-glycoprotein; parathyroid hormone-related protein, cementum-derived growth factor); biogenic proteins and tissue preparations (e.g., collagen, gelatin, extracellular matrix materials and components, carbohydrates, cartilage alginate, platelet rich plasma); gene therapy agents, including naked or carrier-associated nucleic acids (e.g., single- or multi-gene constructs either alone or attached to further moieties, such as constructs contained within a plasmid, viral, or other vector), examples of which include nucleic acids encoding bone-growth-promoting polypeptides or their precursors, e.g., sonic hedgehog protein (see, e.g., P C Edwards et al., *Gene Ther.* 12:75-86 (2005)), BMPs (see, e.g., C A Dunn et al., *Molec. Ther.* 11(2):294-99 (2005)), Runx2, or peptide hormones, or anti-sense nucleic acids and nucleic acid analogs, e.g., for inhibiting expression of bone-degradation-promoting factors; pharmaceuticals, e.g., anti-microbial agents, antibiotics, for example, aminoglycosides, amphenicols, ansamycins, .beta.-lactams, lincosamides, macrolides, nitrofurans, quinolones, sulfonamides, sulfones, tetracyclines, vancomycin, and any of their derivatives, analogues, or combinations thereof, antifungals agents, for example, allylamines, imidazoles, polyenes, thiocarbamates, triazoles, and any of their derivatives, antiviral agents, microbistatic or virustatic agents, anti-tumor agents, for example, e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12), biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, fluorouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, analogues/congeners, derivatives of such compounds, and combinations thereof and immunomodulators, for example, anti-inflammatory agents (steroidal and nonsteroidal anti-inflammatory agents). Exemplary steroidal anti-inflammatory agents include 21-acetoxypregnenolone, alclometasone, algestone, amcinonide, beclomethasone, betamethasone, chloroprednisone, ciclesonide, clobetasol, clobetasone, clocortolone, cloprednol, corticosterone, cortisone, cortivazol, deflazacort, desciclesonide, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, analogues, and combinations thereof. Exemplary nonsteroidal anti-inflammatory agents include, but are not limited to, COX inhibitors (COX-1 or COX nonspecific inhibitors) (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, diclofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and selective COX-2 inhibitors (e.g., diaryl-substituted furanones such as rofecoxib; diaryl-substituted pyrazoles such as celecoxib; indole acetic acids such as etodolac and sulfonanilides such as nimesulide; and metabolism-enhancing factors, e.g., amino acids, non-hormone peptides, vitamins, minerals, and natural extracts (e.g., botanical extracts). The bioactive agent preparation can itself contain a minority of, e.g., processing, preserving, or hydration enhancing agents. Such bioactive agents or bioactive agent preparations can be used in either the porogen particle(s) or the PGD elastomeric polymer material, or both. Where both contain bioactive agent(s), the agent(s) can be the same or different.

In some embodiments, a plurality of different porogen particles can be used, which can differ in any desired ways, e.g., in size, morphology, bulk material, bioactive agent(s), and/or other additives. Porogen particles having the dimensions and characteristics described herein can also be used in combination with "other porogens" that can resorb at a different rate or rates, or that can be of a different size (e.g., nanoparticles) or morphology (e.g., fibrous or filamentous) than the "porogen particles" described herein. Examples of such uses include the use of polymer "porogen particles" along with slower-resorbing DBM particles or with DBM small-particle clusters. Thus, a PGD composite material according to the present technology can comprise a combination of "porogen particles" as defined herein, with "other porogens" known in the art. In some embodiments, at least half of, or at least a majority of, the porogens in a bond graft material according to the present technology can be "porogen particles" having the characteristics as defined herein. In a preferred embodiment, about 60% or more, about 70% or more, about 75% or more, about 80% or more, about 85% or more, about 90% or more, about 95% or more, or about 98% or more of the total volume of porogens in the composition can be comprised of "porogen particles" as defined herein. In some embodiments, at least substantially about all, or about all, or all of the porogens in a composition according to the present technology can be "porogen particles" as defined herein.

In some embodiments in which one or more bioactive agents described above are included in the bulk of a solid particle or core, wall, or layer of a hollow or laminar particle, the additive(s) can make up about 10% or less by volume of the material, about 5% or less, about 4% or less, about 3% or less, about 2% or less, or about 1% or less. The maximal amount of bioactive agent preparation included in a space in a hollow particle can be determined by the volume of the space. The format for additives to be included in porogen particles according to the present technology can be powders, particles, or solutions of any morphology or consistency (e.g., dry, paste, or slurry), provided that the additives can be effectively incorporated into either the bulk substance of the porogen particle or into a void within.

Porogen Particle Parameter Selection

Regardless of the formulation of the biocompatible material selected for a porogen particle, e.g., whatever the identity of a biocompatible biodegradable polymer selected, for use in a given embodiment of the present technology, any of the techniques described in the above-cited references, in the articles cited therein, and in other references known in the art, can be used to obtain approximate biodegradation rates therefore, whether relative or absolute. These rates can then be used to select a dimension for a particular geometry or morphology desired for in vivo biodegradation over a selected time period. For example, where degradation is desired over a period of 3 days, and the desired geometry-plus-morphology is a substantially spherical "solid" microparticle partly embedded in a ceramic- or glass-type matrix and having at least one exposed surface, the particle diameter could be about 220 microns for a polymer that degrades at a rate of about 520 microns per week. Likewise, where a 3-day degradation period is desired for a similarly situated, single-walled hollow microparticle, the wall thickness could be about 20 microns for a polymer that degrades at a rate of about 45 microns per week.

In some embodiments according to the present technology, the biocompatible, biodegradable polymer can be selected in light of other biodegradation-rate influencing factors, to obtain either: porogen particles that contain the polymer, or of a biodegradable polymer and/or bioactive ingredient combination throughout the bulk of the porogen particle (i.e. are neither hollow nor laminar), and which can be biodegraded in vivo within about 10 minutes to about 7 days; or porogen particles that are hollow or laminar particles having at least one wall or layer that is made of the polymer or solid polymer-bioactive ingredient combination, at least one wall of which can be biodegraded in vivo within about 10 minutes to about 7 days, i.e. that average time to dissolution in vivo for the particle or wall is a value within that range. In some embodiments, the polymer or polymeric combination can be selected in conjunction with other particle parameters to obtain porogens in which average time to dissolution in vivo for the particle or wall is within about 10 minutes to about 5 days, or about 10 minutes to about 3 days.

Methods For Making PGD Elastomeric Polymer

In some embodiments, the present technology provides methods for forming PGD elastomeric polymer materials and composites based on PGD elastomeric polymer that are biodegradable, possess dual thermal behavior (plastic-rubber) and shape memory. In some embodiments, to make the PGD elastomeric polymer at room temperature, the following process can be employed: 1) mixing a trifunctional monomer, for example, glycerol and an acid monomer, for example, decane 1, 10 dicarboxylic acid (dodecanedioic acid) in a molar ratio of 5:1 to 1:5, or 3:2 to 2:3, or from 1:2 to 2:1 preferably 1:1. 2) the mixture is then heated to a temperature ranging from about 100° C. to about 150° C., under ambient conditions or under anaerobic conditions, for example, under nitrogen for a period of time ranging from 12 hours to about 48 hours, preferably from about 15 hours to about 30 hours, or from about 18 hours to about 24 hours. 3) The heated mixture is then placed under atmospheric pressure (760 Torrs) or under a vacuum ranging from about 50 mTorrs to about 200 mTorrs, or from about 75 mTorrs to about 150 mTorrs for a period ranging from about 12 hours to about 48 hours, preferably from about 15 hours to about 30 hours, or from about 18 hours to about 24 hours, preferably with constant stirring. The resultant thermosetting cross-linked polyester prepolymer synthesized from glycerol and dodecanedioic acid is called poly(glycerol-dodecanoate).

The resultant PGD prepolymer can then be thermally cured and shaped by placing the viscous PGD prepolymer into a mold and casted into a final shape or configuration. The thermal curing method can include placing the mold containing the PGD prepolymer in a vacuum oven and heated to a specified temperature conducive to thermally cure the PGD prepolymer into the final shaped form i.e. PGD elastomeric polymer. The curing step can be achieved by curing the prepolymer composition at temperatures ranging from about 50° C. to about 500° C., or from about 70° C. to about 300° C. or from about 90° C. to about 150° C. In some embodiments, the thermal curing can occur at a single temperature or it can be stepped by heating the oven to a temperature of 90° C. and then placing the mold containing the PGD prepolymer into the oven at atmospheric pressure (760 Torrs) or preferably under a vacuum (50-150 mTorrs) for a period ranging from about 24 hours to about 72 hours, preferably 48 hours, and then increasing the temperature in the oven to about 100 to about 150, preferably 120 for a period of time ranging from about 24 hours to about 72 hours, preferably 48 hours. Throughout the thermal curing process, a vacuum ranging from about 50 mTorrs to about 200 mTorrs, or from about 75 mTorrs to about 150 mTorrs, preferably 80 mTorrs to about 100 mTorrs, can be applied.

In some embodiments, a PGD prepolymer can have a weight average molecular weight (Mw) ranging between 304 Da. to about 400,000 Da. or from about 304 Da. to about 100,000 Da. or from about 304 Da. to about 50,000 Da. The average molecular weight of a single repeat unit of poly(glycerol dodecanoate) is about 304.37 Da.

In some embodiments, the liquid or solid PGD elastomeric polymer of the present technology can be processed into a wide range of formats and geometries. The PGD elastomeric polymer and the PGD composite materials of the present technology can be shaped into a variety of shapes and configurations. In some embodiments, all of the medical devices, grafts, and materials using PGD elastomeric polymer and/or PGD composite materials can either be porous or non-porous. The porosity can be designed or random.

The soft tissue engineering applications can include PGD elastomeric polymer and/or PGD composite materials shaped into solid or hollow cylinders which may be porous or non-porous, the cylinders ranging in diameter from about 1 mm to about 200 mm, square or rectangular sheets, patches, (e.g. a pericardial patch or a drug-delivery transdermal patch), mesh substrates having pores ranging from about tens of microns to tens of millimeters, beads of various shapes. Other forms that the PGD elastomeric polymer can be fashioned into include: sphere, tube, film, membrane, strand, fiber, filament, coiled strand, capillary network, oval, lenticular, egg-shaped and the like. In some embodiments, the PGD elastomeric polymer and PGD composite materials can be molded using commonly known molding techniques, including, injection molding, compression molding, blow molding, rotational molding, blow-extrusion, profile extrusion, die cutting, casting and other commonly known elastomeric polymer molding techniques, and combinations of all of the above, to create any shape desired in which a mold or die can be made.

In some embodiments, complex shapes can be fashioned using free-form fabrication techniques, including solid free form technology with indirect casting, stereolithography and rapid prototyping methods and combinations thereof using the PGD elastomeric polymer and PGD composite materials having shape memory maintained in the plastic solid when in a non-deformable state. Methods for forming biomedical devices and dental devices and the like using 2D- and 3D micromachining processes can be found in U.S. Pat. No. 7,371,400 Ser. No. 10/038,891 and in U.S. Published Patent Application No. 2006/0154195 Ser. No. 11/301,795, which are both herein incorporated in their entireties. In some embodiments, the solidified PGD elastomeric polymer can be made into a monolithic substrate infused with one or more bioactive agents for the controlled release of drugs, e.g., in joints, cardiac tissue, coronary arteries, wounds or other mechanically dynamic environments The shape of the compositions and materials of the present technology can be manipulated for specific tissue engineering applications as well as other applications. Exemplary PGD elastomeric polymer and/or PGD composite material shapes or configurations can include particles, tubes, spheres, strands, coiled strands, films, sheets, fibers, patches, membranes or and combinations thereof. In some embodiments, microfabrication can be used to form capillary networks from compositions and materials of the present technology. For example, a silicon wafer is processed using standard microfabrication techniques to produce a capillary network having a desired pattern. The network is coated with a sacrificial layer, for example, sucrose. The PGD prepolymer can be cast over the sacrificial layer and thermally cured according to a method described herein. Water can be used to dissolve the sacrificial layer and release the polymerized compositions and materials of the present technology, which will have a relief pattern of the capillary networks that had been formed in the silicon wafer. In some embodiments, the channels in the PGD elastomeric polymer and/or PGD composite compositions of the present technology can measure from about 2-10 μm across and from about 2-8 μm deep. It is to be understood, that while the size limit for the channels is dictated by the resolution of the microfabrication technique, biological applications may benefit from channel sizes on the order of 5 to 10's or 100's of microns or larger. The capillary networks can be closed by covering them with a flat sheet of PGD elastomeric polymer and curing it. For example, a layer of uncrosslinked PGD polymer can be used as a "glue" between the patterned layer and the flat layer. Polymerizing the "glue" can knit the two pieces together.

These shapes can be exploited to engineer a wide variety of tissues. For example, the polymer can be fabricated into a tube to facilitate nerve regeneration. The damaged nerve is fed into the end of the tube, which guides the migration of axons across the wound site. In some embodiments, PGD compositions and materials of the present technology can be used to fabricate the tissue structures of liver and other organs such as the heart, esophagus, stomach, intestines and kidneys. For example, formed into a network of tubes that mimic a blood vessel and capillary network which can be connected to a nutrient supply to carry nutrients to the developing tissue. Cells can be recruited to the network of tubes in vivo, and/or it can be seeded with blood vessel cells. Around this network of tubes, compositions and materials of the present technology can be formed into networks imitating the arrangements of extracellular matrix in liver tissue and seeded with hepatocytes. Similarly, some embodiments of the PGD elastomeric polymer compositions and composite materials of the present technology can be fabricated into a fibrous network, seeded with islet cells, and used to tissue engineer a pancreas-like tissue. The compositions and materials of the present technology can also be seeded with a variety of other cells, for example, tenocytes, fibroblasts, ligament cells, endothelial cells, epithelial cells, muscle cells, nerve cells, kidney cells, bladder cells, intestinal cells, chondrocytes, bone-forming cells, adipocytes, stem cells such as human embryonic stem cells, adipose derived mesenchymal stem cells, mesenchymal stem cells, and others.

Methods for Use and Applications

Due to its elastomeric and shape retention nature, the compositions and materials of the present technology can find application in a wide variety of applications including tissue engineering of tissues, especially muscle tissue, artery, nerves, heart valves, intestinal structures, vocal chords and any elastic structure in the body of a mammalian or other animal subject, including humans. In some embodiments, the PGD elastomeric polymers and PGD composite materials can be used to manufacture biomedical devices, medical devices and tissue substrates that are designed to repair, fill, augment and replace defective tissue. In some embodiments, the medical device can include a graft and/or implant to facilitate tissue repair and/or regeneration Defective tissue or tissue defects can include injured, traumatized, diseased and hyperplastic tissue that has occurred as a result of trauma, infection, congenital defect and disease. Exemplary tissue defects include blood clots, atherosclerotic plaques, heart valve defects, aneurisms, wounds, collapsed vessels, tumors, torn muscles, torn tendons, torn ligaments, infected tissue, deinnervated muscle tissue, infected bones, bone fractures or cardiac tissue necrosis.

For example, in some embodiments, a biodegradable PGD elastomeric polymer and/or PGD composite materials thereof can be used in the formation of medical devices, for example, medical devices that are intravascular, i.e. that can be inserted into blood vessels, the heart, capillaries, lymph, and any other tubular structure that has an internal lumen, for example, tubes, e.g., for obliteration of intra and extra cardiac defects. (i.e. ASD, VSD, anomalous vessels) but also fistulas, and aneurismatic vessels, for example cardiac stents, including, cutting stents and stents for balloon deployment. In some embodiments, the medical devices of the present technology can be delivered using delivery devices in vivo, for example, surgical instruments for affixing tissue grafts and the like, laparoscopic instruments, catheters and guide wires. Preferably, the delivery device is constructed to withstand pressure of the surrounding tissue and guide the medical device or tissue replacement, substantially unhampered by obstacles, such as scar tissue formation. In tissue regeneration applications, the PGD elastomeric polymer composition be functionalized (e.g., with one or more bioactive agents, for example a growth factor, TGF-beta, IGF, PGDF, GRGD and the like) to facilitate the attachment and guidance of target cells, e.g. stem cells, endothelial cells, epithelial cells, neurons, cardiomyocytes, bone forming cells (osteoblasts and osteogenic progenitor cells), chondrocytes, nerve cells and the like. In still other embodiments, the PGD elastomeric polymer and/or PGD composite materials can also in addition to or in lieu of functionalization with growth factors or differentiation factors, be a reservoir for pharmaceutical agents, drugs and medicaments for targeted drug delivery into the tissue/graft replacement site.

In some embodiments, PGD elastomeric polymer can be used to fabricate "Amplatzer"-like medical devices, for obliteration of intra and extra-cardiac defects. (i.e. atrial septal defects (ASD), ventricular septal defects (VSD), anomalous vessels) but also include fistulas, and aneurismatic vessels.

The Amplatzer-like medical device or an Rashkind double umbrella device can be folded and inserted/loaded into a delivery device (for example, a laparoscope or catheters similar to catheters deployed for coronary stent placement) and positioned in vivo to a tissue defect site (e.g. a heart septal defect site) with a minimally invasive procedure. Once in place the device in contact with warm blood assumes its deployed final shape.

In some embodiments, biodegradable PGD elastomeric polymer compositions and materials of the present technology can be used as a matrix, scaffold, or structure for cell attachment and/or encapsulation. In some embodiments, short-peptides which are bioactive (e.g., GRGD) can be incorporated into the cured PGD elastomeric polymer to enhance cell activity, including, cell adhesion. Incorporation of these short peptides into the PGD elastomeric polymer can be achieved by mixing the functionalized peptides with the PGD prepolymer followed by curing. In some embodiments, when the bioactive agent is thermally labile, the bioactive agent can be sprayed, coated, sputtered and applied in any known form thus retaining the activity of the bioactive agent onto the device/graft and/or in any lumen, aperture or pore contained by the device/graft. Optionally, the PGD composite materials may contain bioactive agents encapsulated within a biodegradable polymer. The encapsulated bioactive agent can be added to the PGD prepolymer or added to the device graft. In some embodiments, the surface of the device/graft comprising the PGD elastomeric polymer and/or PGD composite material can be nano-patterned, e.g. on the inside of the tube or cylinder, to guide cells. Such an application can apply to a nerve graft, wherein the PGD elastomeric material can be nano-patterned to enhance the cell guidance over the nerve graft and guide neurons and/or Schwann cells.

In some embodiments, the present inventions provide biodegradable PGD elastomeric compositions and materials as a 3D matrix for the encapsulation and proliferation of cells. In some embodiments, these matrixes are configured for stem cells.

To make solid sheets of PGD elastomeric polymer, a sample of viscous PGD prepolymer can be layered on a flat mold of PTFE, and thermally cured as described above. Sponges are variations of the sheets, where the prepolymer solution is mixed with a salt of the desired size in a 1:1 weight ratio, and poured onto the PTFE mold and thermally cured as described above. At the end of the thermal curing process, the salt is leached out leaving behind a highly porous PGD elastomeric polymer sponge having a porosity of at least about 20%, 30% 40%, 50%, 55%, 60%, 65%, 70%, 75%, 80%, 85%, 90%, 92%, 94%, 96%, 98%, and at least 99%. In some embodiments, the PGD elastomeric polymer sponge has a porosity ranging from about 20% to about 60%, or from about 65% to about 90% or from about 70% to about 80%. The sizes of the pores in the PGD elastomeric polymer sponge can range from about 5 microns to about 500 microns.

In some embodiments, the present technology provides biodegradable PGD elastomeric polymer compositions and PGD composite materials in the form of a 3 dimensional matrix for the growth and proliferation of cells. In some embodiments, these matrices can be configured for the growth and/or differentiation of stem cells.

For example, in some embodiments, a solid porogen as described herein, consisting of a biocompatible, biodegradable and non-toxic polymer can be used to form a porous network within the PGD composite material. The PGD elastomeric polymer can be mixed with the biocompatible and biodegradable polymer porogens followed by thermal curing to form the composite material. Upon degradation of the porogen, the PGD composite material can then infused with cells and provide a scaffold in which the cells can grow and proliferate within the PGD composite material. The PGD composite material containing the embedded porogen/cells can then be submersed in a growth medium that may be utilized for the desired growth and/or differentiation of the embedded cells, e.g. stem cells.

The porous scaffolds show a minimal degradation rate in vitro and in vivo and can maintain its 3-D structure for up to 12-24 months. In some embodiments, other cell types can also be added to the PGD porous composite scaffold embedded with a first cell type to encourage the growth and proliferation of one or more different cell types requiring support cells, for example, certain immune cells require the establishment of supporting cells such as stromal cells and the like. The PGD porous composite scaffold can be used to support and grow hematopoietic cells, neurons, hepatocytes, immune cells (e.g. granulocytes, lymphocytes, dendritic cells, platelets etc), muscle cells, cardiomyocytes, endothelial cells, epithelial cells and any cell type derived from autogenic, allogeneic and xenogeneic sources.

In some embodiments, the present technology provides bone and cartilage graft materials that can include PGD elastomeric polymer substrates and/or PGD composite materials having bone replacement qualities operable to induce the growth of bone cells and/or chondrocytes at the site of implantation. In some embodiments, the PGD composite material can include a porogen particle comprising a calcium ceramic as known in the art of bone graft materials. In some embodiments, the calcium ceramic can include calcium sulfate, calcium phosphate, hydroxyapatite, calcium carbonate, calcium sulfate carbonate and combinations thereof. In addition, the PGD composite material for use as a bone or cartilage graft can also include one or more bioactive agents that encourage the growth and/or differentiation of osteogenic cells, and/or chondrocytes for the formation of de-novo bone and/or cartilage at the site of a bone and/or cartilage defect. The PGD elastomeric polymer and PGD composite materials can also be layered with a population of osteogenic cells and/or chondrocytes on at least one surface and implanted into a bone or cartilage defect site for the replacement, augmentation and growth of bone and/or cartilage, such as a tendon or ligament.

In some embodiments, for example, bioactive agents, including one or more growth factors, anti-inflammatory agents, antimicrobial agents can be incorporated into a wound dressing/sealant comprising a PGD elastomeric polymer composition and/or PGD composite material of the present technology, for example a bandage, a strip of PGD elastomeric polymer, a mesh, a sponge, a membrane and the like, to recruit cells to a wound site and/or promote specific metabolic and/or proliferative behavior in cells that are at the site and/or seeded within the matrix. Exemplary growth factors include, without limitation, TGF-beta, acidic fibroblast growth factor, basic fibroblast growth factor, epidermal growth factor, IGF-I and II, vascular endothelial-derived growth factor, bone morphogenetic proteins, platelet-derived growth factor, heparin-binding growth factor, hematopoietic growth factor, and peptide growth factor. In some embodiments, integrins and cell adhesion sequences (e.g., the RGD sequence) can be attached to the compositions and materials of the present technology to facilitate cell adhesion. In some embodiments, extracellular matrix components, e.g., collagen, fibronectin, laminin, elastin, etc., can be combined with PGD elastomeric polymer compositions and PGD composite materials of the present technology to manipulate cell recruitment, migration, and metabolism and the degradation and mechanical properties of the material. In some embodiments, proteoglycans and glycosaminoglycans can be covalently or non-covalently attached to the PGD elastomeric polymer compositions and PGD composite materials of the present technology.

Tissue Engineering Applications

The elasticity and ability to "tailor" the chemical and physical properties of the PGD elastomeric polymer compositions and PGD composite materials of the present technology lends to the use of these compositions and materials in some embodiments, in regenerating a variety of tissues. In some embodiments, for example, the PGD elastomeric polymer compositions and PGD composite materials of the present technology can be used to tissue engineer, epithelial, connective, nerve, muscle, organ, and other tissues, as well as artery, ligament, skin, tendon, kidney, nerve, liver, pancreas, bladder, and other tissues. In some embodiments, compositions and materials of the present technology can be used as the template for mineralization and formation of bone.

Tissues typically experience mechanical forces and deformation in daily use, and tissue remodeling is often influenced by mechanical forces. For example, heart and other muscle will increase in density and size when they are frequently used and will atrophy under disuse. Mechanical force stimulates the cells that produce extracellular matrix elements to produce growth factors that promote either the production or degradation of ECM. The use of a PGD elastomeric polymer composition and PGD composite material of the present technology, that is biocompatible, biodegradable, exhibits shape memory properties, linear elastic behavior at room temperature, and non-linear elastic behavior at body temperature is highly desirable in the context of tissue replacement. These characteristics make this material especially attractive for creating surgically implantable tissue engineered scaffolds. The mechanical behavior and degradation pattern of PGD elastomeric polymers can both be altered by varying the glycerol:dodecanedioic acid molar ratios, and curing conditions. The resultant artificial tissue mimics the normal physiological response to mechanical forces of the tissue it replaces. These artificial tissue constructs/grafts can optionally be seeded with cells and can facilitate the regeneration of normal tissue, as mechanical stimulation can be applied to the early in the culturing of these tissue engineered constructs.

In some embodiments, the medical device to be implanted into a subject in need of soft tissue repair can include a PGD containing matrix-based autologous chondrocyte implantation (MACI) device. Other medical devices can include tissue grafts that include a matrix or cartilage plug for use with either microfracture or mosaicplasty techniques for repair of articular cartilage.

For example, some embodiments of PGD elastomeric polymer compositions and PGD composite materials of the present technology can be used to tissue engineer or regenerate a portion of a patient's bladder. In some embodiments, smooth muscle cells and urethral epithelial cells are seeded onto compositions and materials of the present technology. The cells can be allowed to proliferate before the implant is placed into a patient. To replace or regenerate cartilage, chondrocytes can be seeded onto some embodiments of the compositions and materials of the present technology, which can withstand the cyclic shear and compressive forces cartilage is subjected to as joints bend.

Similarly, in other embodiments, other internal organs having a peristaltic contraction functionality can be partially treated by replacement of defective peristaltic tissue with the PGD elastomeric polymer compositions and PGD composite materials of the present technology. For example, intestinal tissue, particularly the regions of the small or large intestine that are diseased due to inflammation and/or infection can be removed and replaced with bioequivalent tubular tissue engineered constructs comprising PGD elastomeric polymer compositions and PGD composite material having layered cell populations of one or more of smooth muscle, epithelial cells and other cell types that may function in passing nutrients and wastes through the intestine. Such a tissue engineered graft may find utility in Crohn's disease, irritable bowel syndrome, ulcerative colitis, enteritis, and other similarly related inflammatory and/or infectious diseases of the gastro-intestinal tract. Other tissues or portions thereof, such as the stomach and the esophagus may be replaced with PGD elastomeric polymer compositions and PGD composite materials of the present technology seeded optionally with cells and/or coated with one or more bioactive agents for the treatment of chronic heart burn, ulcers and esophageal cancer.

In some embodiments, PGD elastomeric polymer compositions and PGD composite materials of the present technology may also be used to produce prosthetic heart valves. Heart valves implanted in vivo can be very flexible and are subjected to cyclic deformation as the heart beats. The body repairs tears in heart valve through normal physiologic mechanisms and thus can regenerate heart valves made of biodegradable materials. In some embodiments, the present technology provides PGD elastomeric polymer compositions and PGD composite materials formed in the shape of a heart valve for example, a trileaflet heart valve, and seeded with smooth muscle cells and endothelial cells to facilitate remodeling in the body to produce a new, non-synthetic heart valve. The tissue engineered heart valves of the present technology permit implantation of replacement heart valves with a thromboresistant surface and a viable interstitium with repair and remodeling capabilities. The cells that are to be seeded on the surface of the PGD elastomeric polymer compositions and PGD composite materials can include autologous marrow stromal cells, mesenchymal stem cells, adipose derived stromal cells and vascular stem cells. The heart valves of the present technology seeded with the above autologous cells provide excellent functional performance and strong resemblance to natural heart valves as to morphological and biomechanical features. In some embodiments, it may be desirable to add fibroblasts and one or more bioactive agents to prevent thrombosis. In some embodiments, the regeneration of cells occurs over a period of 2-6 months, where the degradation rate of the polymer can be controlled by modifying the proportion of glycerol, dodecanedioic acid or both.

In some embodiments, a cardiac 3D trileaflet valve can be made with an indirect solid free form fabrication using the PGD elastomeric polymer material as the feed material and shown in FIG. 5A-5D. The trileaflet valve made in accordance with the materials disclosed herein can be implanted into the heart of a subject having heart valve disease or one requiring a new heart valve as a result of cardiovascular disease. The trileaflet valve can open and close in unison with the flowing of blood through the aorta. The PGD polymer material is biocompatible and durable in bodily implant applications.

Medical Applications

Other medical applications may also benefit from the elasticity of the PGD elastomeric polymer compositions and PGD composite materials of the present technology when implanted in a subject in need thereof. For example, after abdominal surgery, the intestines and other abdominal organs tend to adhere to one another and to the abdominal wall. It is thought that this adhesion results from post-surgical inflammation, however, anti-inflammatory drugs delivered directly to the abdominal region dissipate quickly. In some embodiments, PGD elastomeric polymer compositions and PGD composite materials of the present technology can be used to deliver anti-inflammatory drugs to the abdominal region. Because the PGD elastomeric polymer compositions and PGD composite materials of the present technology can be provided in embodiments that are soft and flexible at 37 degrees or body temperature, yet biodegradable, they can be implanted between the abdominal wall and internal organs, for example, by attaching it to the abdominal wall, without cutting internal organs, which would lead to infection. The anti-inflammatory drug can be released from the PGD elastomeric polymer compositions and PGD composite materials of the present technology over a period of time, e.g., greater than 2-6 months. While previous researchers have attempted to use hydrogels, hyaluronic acid-based membranes, and other materials to solve these problems, such materials tend to degrade quickly in the body; a longer resident period is necessary to prevent adhesion.

In some embodiments, PGD elastomeric polymer compositions and PGD composite materials of the present technology can be used to coat a metallic stent. Because PGD elastomeric polymer compositions and PGD composite materials of the present technology can be provided in embodiments that are flexible, specifically at body temperatures, it will expand with the stent without ripping, while the stiffness of the metal stent will prevent the PGD elastomeric polymer compositions and PGD composite materials of the present technology from elastically assuming its previous shape. The compositions and materials of the present technology can include one or more bioactive agents, for example one or more anti-coagulant and/or anti-inflammatory agents to facilitate preventing, e.g., the formation of clots or scar tissue. Angiogenic agents can be included to promote the remodeling of the blood vessel surrounding the stent.

In some embodiments, PGD elastomeric polymer compositions and PGD composite materials of the present technology can also be used to prepare "long term" medical devices. Unlike typical permanent medical devices, compositions and materials of the present technology can be made to degrade over time, for example, they can be fabricated into a biodegradable cardiac stent. In some embodiments, the PGD elastomeric polymer compositions and PGD composite materials of the present technology acts as a plasticizer that enables the stent to expand into the desired shape after implantation. The stent increases the diameter of the blood vessel to allow easier circulation, but, because the stent is biodegradable, surrounding blood vessels increase in diameter without thrombosis or covering the stent with scar tissue, which could reclose the blood vessel. The time the stent should remain in place and retain its shape before degradation will vary from patient to patient and depend partially on the amount of blockage and the age of the patient (e.g., older patients require more time to heal). Using the teachings presented herein, one of ordinary skill in the art can adjust one or more of, e.g., the DA, the cross-link density, and the proportion of glycerol to dodecanedioic acid to adjust the degradation rate. As for the coated stent, a degradable stent of the present technology can also release biomolecules, bioactive agents, or some combination of these in situ.

In some embodiments, compositions and materials of the present technology can be used to support in vivo sensors and catheters. The PGD elastomeric polymer compositions and PGD composite materials of the present technology can be constructed into a chamber for an optical fiber-based sensor or a coating for a catheter that is inserted into the area of interest. In a sensor, the chamber can contain a specific chromophore-bonded receptor for the molecule of interest. When an analyte attaches to the receptor, the chromophore will either emit or absorb light at a specific wavelength. The absorption or emission may be detected by an apparatus connected to the optical fiber. The sensor may be used for, for example, short term, continuous monitoring, for ten to fifteen days. Likewise, a catheter may be used to periodically deliver drugs or other small molecules or bioactive agents to a specific site or intravenously. Use of some embodiments of the PGD elastomeric polymer compositions and PGD composite materials of the present technology can reduce the formation of scar tissue which would ordinarily form around a shunt or other implant that is used for more than two weeks. It is preferred, in some embodiments, the degradation rate of the compositions and materials of the present technology are chosen so that there is no significant degradation of the material while it is in place in the patient.

PGD elastomeric polymer could be successfully deployed for fabrication of an Intra-Uterine Device (IUD). Such device could be folded for an easy insertion and once placed in-situ, it would assume the correct shape. It would be soft and pliable therefore with minimal risk of perforation or discomfort for the patient; being biodegradable, it would not require a second procedure for removal. Other applications could be for spinal disc or articulating surface repair using PGD devices that are formed and then compacted at room temperature but then expand when brought in contact with tissues and heated to body temperature. PGD, either as an injectable suspension or as small devices embedded with pro-inflammatory molecules (interferon, etc), could be used for obliteration of cavities (i.e. pleurodesis) once in place the PGD device would cause a localized inflammatory reaction creating a local fibrous reaction and ultimately obliteration.

Drug Release Applications

In some embodiments, PGD elastomeric polymer compositions and PGD composite materials of the present technology can be used for drug release applications, for example, in applications where the matrix retaining the drug needs to be flexible. Because the PGD elastomeric polymer compositions and PGD composite materials of the present technology can provide embodiments that are elastic, they can move with the patient as he/she walks, runs, sits, etc. The PGD elastomeric polymer compositions and PGD composite materials of the present technology can provide embodiments that maintain their mechanical integrity as they degrade, the tissue engineered device may be less likely to fail catastrophically toward the end of its lifetime, reducing the risk of a bolus release of the desired agent. Biomolecules and bioactive agents can all be combined with some embodiments of the PGD elastomeric polymer compositions and PGD composite materials of the present technology embedded in porogen particles or alternatively applied to at least one surface of the PGD elastomeric polymer material and/or PGD composite material. The bioactive agent can be non-covalently attached to the surface of the PGD elastomeric polymer material and/or PGD composite material via hydrogen bonds, electrostatic interactions, hydrophobic interactions, and van der Waals interactions.

In some embodiments, PGD elastomeric polymer material and/or PGD composite material of the present technology can also be used for other wounds that are hard to close or that fail to heal properly through normal physiologic mechanisms. For example, diabetics often get skin injuries ("diabetic ulcers"), especially in the lower extremities that take a long time to heal or fail to heal properly due to poor circulation. The use of some embodiments of the PGD elastomeric polymer material and/or PGD composite material of the present technology to deliver antibiotics or anti-inflammatory agents to these wounds can aid healing and provide a cover for the wound.

Methods in accordance with the present disclosure for repairing a soft tissue defect can include providing an elastomeric PGD polymer and administering the elastomeric polymer to a soft tissue defect site such as in a cartilage defect obtained either through disease, trauma or congenitally deformed. In some embodiments, the soft tissue defect can include an intervertebral disc defect requiring intervertebral disc replacement.

In some embodiments, some of the applications capable from benefiting from the use of the PGD elastomeric polymers can include: orthopedic and cranio-facial reconstruction and healing of cartilage and other soft musculoskeletal tissues (ligaments, tendons, intervertebral discs, meniscus and the like), cardiovascular repair and augmentation (blood vessels and cardiac scaffolds) and peripheral nerve repair. In some embodiments, the soft tissue defect is cartilaginous, fibrocartilaginous, cardiovascular or other soft tissues and the PGD material is manufactured within a desired structural shape with a desired microstructure.

Non-Medical Applications

In some embodiments, the PGD elastomeric polymer can be incorporated into a variety of non-medical products that use thin sheets, membranes and patches of synthetic elastomeric materials. The present PGD elastomeric polymer has the advantage of shape memory and is completely biodegradable and biocompatible. Hence, articles such as plastic bags, e.g. shopping bags, trash bags and the like can be made primarily from or at least contain a significant amount of the present PGD elastomeric polymer. Other articles that can be manufactured from the present compositions can include: bandages, band aids, sanitary napkins, incontinence protectors, diapers, female hygine products, prophylactics, packaging containers for food and other perishable articles Commercial Packages A commercial package can provide a PGD elastomeric polymer according to the present technology as a pre-moistened paste or other semi-solid or liquid formulation; as a hardened solid part or substrate, or it can provide the PGD elastomeric polymer as a dry powder. Where the PGD elastomeric polymer is supplied in a solid form, an aqueous solution can be provided in the commercial package for use in wetting the solid material. A commercial package can contain instructions for use, and optionally for further preparation of the PGD elastomeric polymer prior to use, for example, when a tissue replacement is needed a sheet, membrane, patch or scaffold member comprising the PGD elastomeric polymer can be cut to the approximate shape needed for in vivo implantation. The commercial package can optionally contain a device or devices for use in cutting, shaping, and/or administering (e.g., inserting, injecting, or applying) the PGD elastomeric polymer.

EXAMPLES

Example 1

Polymer Fabrication And Characterization

The polymer was fabricated from glycerol (MP Biomedical, LLC, Solon Ohio) and dodecanedioic acid (Sigma-Aldrich, Minn.) in 1:1 molar ratio.

Both elements were mixed together in a three-necked flask at 120° C. flask under nitrogen and stirring conditions for 24 hours. After this time the mixture is placed under vacuum (100 mTorrs) and continuous stirring for 24 hours and cured using a thermal curing method. In one example of thermal curing, the pre-polymer, thick and viscous at this stage, can be casted in a variety of molds. Mold and pre-polymer are transferred into a vacuum oven at 90° C. for 48 hrs, at the end of which the temperature is raised to 120° C. and kept such for 48 hrs; vacuum is pulled and maintained at 90 mTorrs for the whole duration of the thermal curing process.

Polymer was made from a 1:1 molar ratio mixture of glycerol and dodecanedioic acid. Tensile tests were performed on cured specimens in compliance with the ASTM D412 standard. Strain at break (SAB), and modulus acquired at four different ambient temperatures (25, 34, 37, 42° C.) (n=20). In some embodiments, alternate ratios of glycerol: dodecanedioic acid are contemplated to achieve different SAB and modulus results. In some embodiments the polymer material comprising glycerol and dodecanedioic acid, can include ratios of glycerol to dodecanedioic acid ranging from about 10:1 to about 1:10.

Direct scanning calorimetry (DSC) and thermogravimetric analysis (TGA) also performed on cured PGD specimens (n=20). In-vitro biocompatibility was assessed by seeding ovine artery fibroblasts on Petri dishes, coated with 1% PGD and observed under microscope daily for two weeks. In-vitro degradation was assessed by soaking specimens (n=20) in PBS at 37° C. and measuring their dry weight after 20, 40, 60 and 90 days.

Data were expressed as a median and range. ANOVA with Tukey HSD was used to compare means between groups (p<0.05). Degradation data was fit to a linear regression model to estimate the polymer half-life.

TABLE 1

Modulus and strain break of the PGD polymer in accordance with the present disclosure at 25° C. and 37° C.

| Temperature | Modulus (MPa) | SAB % |
| --- | --- | --- |
| 25° C. | 136.55 (67.2-155.7) | 225 (192.1-243.5) |
| 37° C. | 1.08 (0.25-2.6) | 123.2 (62.9-163.6) |

A statistically significant difference was found between specimens tested at 25° and 37° C. Modulus and SAB are summarized in table 1. Stress-strain plots show a plastic and elastomeric behavior at 25 and 37° C. respectively. (FIGS. 3A and 3B) DSC confirmed a glass transition temperature of 32.1° C. (31-34.2° C.); no melting point was detected with TGA. PGD allowed cell growth with a confluence of 70-75% after a week in culture. The estimated PGD half-life in PBS at 37° C. was 16 months Example 2

Chemo-Physical Properties

Molecular calculations (elemental composition and density p) were performed with ChemDraw software (ACDLabs, Toronto Canada). Density was also calculated experimentally with Archimedes technique. Cured samples were cut into 10 pieces in order to determine if the density was uniform across the sample, and each measurement taken in duplicate. Each sample was soaked in deionized water (reverse osmosis) for 24 hours to ensure water penetration into pores. Two measurements were obtained and used according to the equations: $W_{dry}$ (the dry weight of the sample) and $W_{sub}$ (the weight of the sample submersed in water), where $$Volume_{apparent} = \frac{W_{dry} - W_{sub}}{\rho_{water}} \quad (Eq. 1)$$

$$Density_{apparent} = \frac{Mass_{dry}}{Volume_{apparent}} \quad (Eq. 2)$$

The cross-linking density (moles of active network chain per unit volume) was calculated from the following basic equation that relates the retraction stress σ, to its extension ratio α:

$$\sigma = nRT\left(\alpha - \frac{1}{\alpha^2}\right) \quad (Eq. 3)$$

where σ is the stress measured and $\alpha = L/L_0$.
The cross-linking density n is also expressed as:

$$n = \rho/M_C \quad (Eq. 4)$$

And from Eq. 3 we can derive $M_c$ (the number-average molecular weight between cross-links).

Elemental composition of the repetitive unit is: (calculated for $C_{15}H_{28}O_6$) C=59.19%, H=9.27%, O 31.54%. Its calculated average mass is 304.37 Da. Calculated density was 1.128±0.06 g/cm³, close to the experimental data of 1.131±0.010 g/cm³. Cross-linking density n, calculated from Equation 1 was 1.35±0.2×10⁴ mol/cm³ and $M_c$ (the number-average molecular weight between cross-links) was 8466±1180 g/mol.

Example 3

Fourier Transform Infrared, Thermogravimetric and Differential Scanning Colorimetry Analysis of PGD Elastomeric Polymers FTIR was performed on a Spectrum BX FTIR system (Perkin Elmer Inc. Waltham, Mass.), equipped with an Attenuated Total Reflectance (ATR) accessory (Perkin Elmer Inc. Waltham, Mass.). Small slabs of fully cured and uncured polymer were tested. Thermogravimetric analysis (TGA) was performed on a Perkin Elmer TGA (Perkin Elmer Inc. Waltham, Mass.) and the samples were tested in the range from 25 to 900° C. (n=20). Differential Scanning Calorimetry (DSC), was performed on a Perkin Elmer DSC 7 (Perkin Elmer Inc. Waltham, Mass.). Specimens were tested from 25 to 60° C. (n=20) We analyzed data from both DSC and TGA with Pyris software (Perkin Elmer Inc. Waltham, Mass.). Reaction between glycerol and dodecanedioic acid in a 1:1 molar ratio yields an elastomer that is soft and pliable out of the oven, hardening upon cooling at room temperature. We anticipated that formation of PGD occurred by polycondensation of glycerol and dodecanedioic acid. Fourier Transformed Infra-Red (FTIR) on pre-polymer slabs confirmed a broad OH stretch, at 3331 cm⁻¹, partially masking a methyl stretch at 2927 cm⁻¹. (FIG. 2A). On fully cured slabs the O—H stretch at 3331 cm⁻¹ is absent unmasking the methyl stretch at 2927 cm⁻¹, and an intense C=O stretch, indicative of esteric bonds, appears at 1735 cm⁻¹ (FIG. 2B).

Thermogravimetric analysis (TGA) shows no melting point in the range from 25 to 900° C., with PGD undergoing a complete combustion at about 700° C. Differential scanning calorimetry (DSC) confirms a glass transition temperature ($T_g$) of 32.1° C. (31-34.2° C.).

Example 4

Tensile Measurements and Curve Fitting

We cast the pre-polymer into dog-bone shaped strips, according to the ASTM standard D 412. The specimens (n=20) were placed in a MTS tensile machine (MTS System Corp. Eden Prairie, Minn.) equipped with a 500 N load cells, a tensile grip system (MTS System Corp. Eden Prairie, Minn.), and a custom-built environmental chamber. The environmental chamber was equipped with two temperature probes one to measure the temperature of the chamber, the other in direct contact with the specimen. The temperature inside the chamber was regulated by means of a thermocontroller (Cole-Parmer Instrument Co. Vernon Hills Ill.) receiving input from the two probes and driving a heating element (Watlow, St. Louis, Mo.) placed inside the chamber to the desired temperature. Deflection rate was kept at 50 mm/min. The specimens were tested to failure at 21, 32, 37 and 42° C.

We fit the data obtained from tensile tests (strain and stress) at 37° C. to a one-term Ogden constitutive model for hyperelastic materials using Matlab software (The MathWorks, Natick, Mass.). The one term Ogden model is based on a strain energy function of the form:

$$W(\lambda_1, \lambda_2, \lambda_3) = \frac{\mu_1}{2}(\lambda_1^{\alpha_1} + \lambda_2^{\alpha_1} + \lambda_3^{\alpha_1}) \quad \text{(Eq. 5)}$$

Where W is the strain energy function, $\lambda_i$ denote the stretch ratios in the $x_1$, $x_2$ and $x_3$ directions, and $\mu_i$ and $\alpha_i$ are constants that are fit to experimental data. The resulting 1$^{st}$ Piola-Kirchoff stress is calculated as:

$$T_i = -\frac{1}{\lambda_1}p + \frac{\partial W}{\partial \lambda_i} \quad \text{(Eq. 6)}$$

Where $T_i$ is the 1, 2 or 3 normal component of the 1$^{st}$ Piola-Kirchoff stress and p is the hydrostatic pressure. For the uniaxial tensile test in this study, the hydrostatic pressure p can be calculated from the fact that stresses on the specimen face perpendicular to the test direction are zero. Assuming the specimen is tested in the $x_3$ direction, this leaves the final expression for the 1$^{st}$ Piola-Kirchoff stress as:

$$T_3 = -\frac{1}{\lambda_3\sqrt{\lambda_3}}\mu_1\sqrt{\frac{1}{\lambda_3}}^{\alpha_1-1} + \mu_1\lambda_3^{\alpha_1-1} \quad \text{(Eq. 7)}$$

The 1$^{st}$ Piola-Kirchoff stress is calculated from the experimental tensile test by dividing the applied force by the initial specimen area. The coefficients from the model (Eq. 7) are then fit in a least squares sense to the experimental stress using the unconstrained optimization routine fminunc from the MATLAB optimization toolbox. Coefficient of determination value ($R^2$) was calculated for the fit. In addition, the Baker-Eriksen inequality was assessed and found to be satisfied for each fit $$\left(\lambda_3 \frac{\partial W}{\partial \lambda_3} - \lambda_2 \frac{\partial W}{\partial \lambda_2}\right)(\lambda_3 - \lambda_2) > 0 \quad \text{(Eq. 8)}$$

Figure 3A:
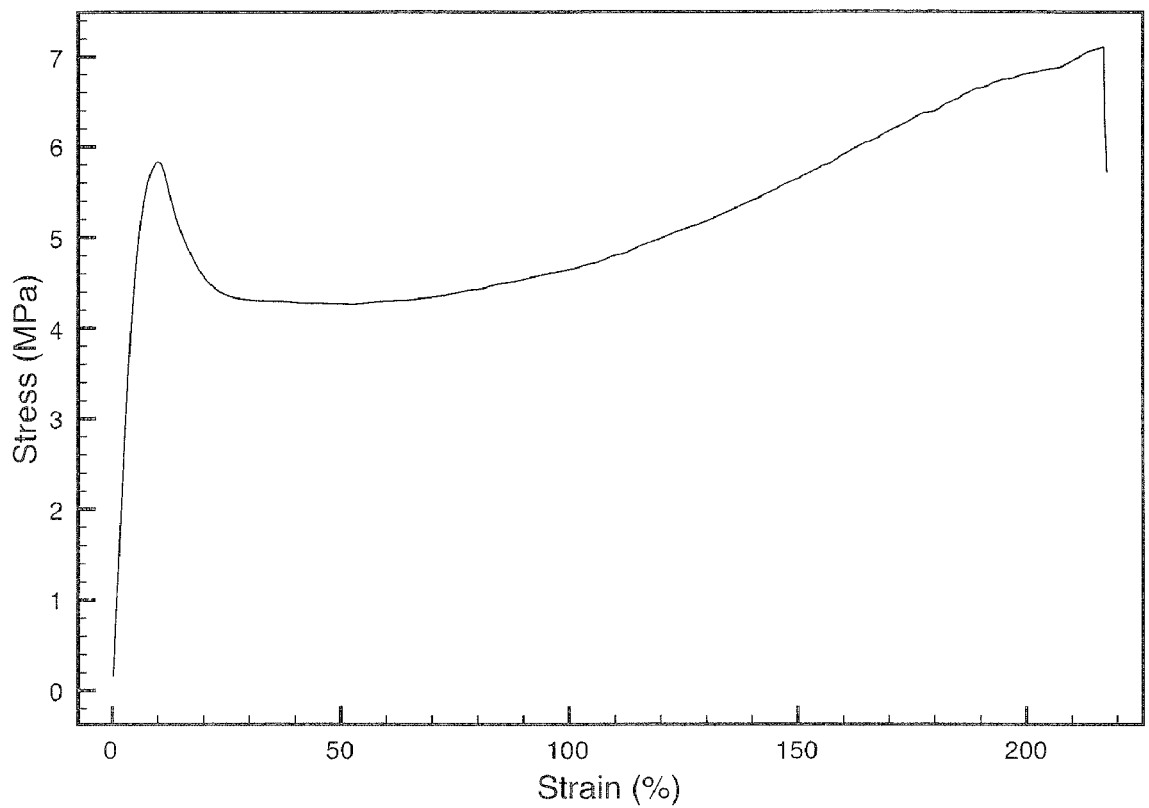
FIG. 3A is a graphical plot of the relationship between stress measured in MPa versus strain measured as a percentage of the PGD elastomeric polymer at 21° C. illustrating a curve being representative of a tough plastic material in accordance with the compositions and methods of the present disclosure.
Figure 3B:
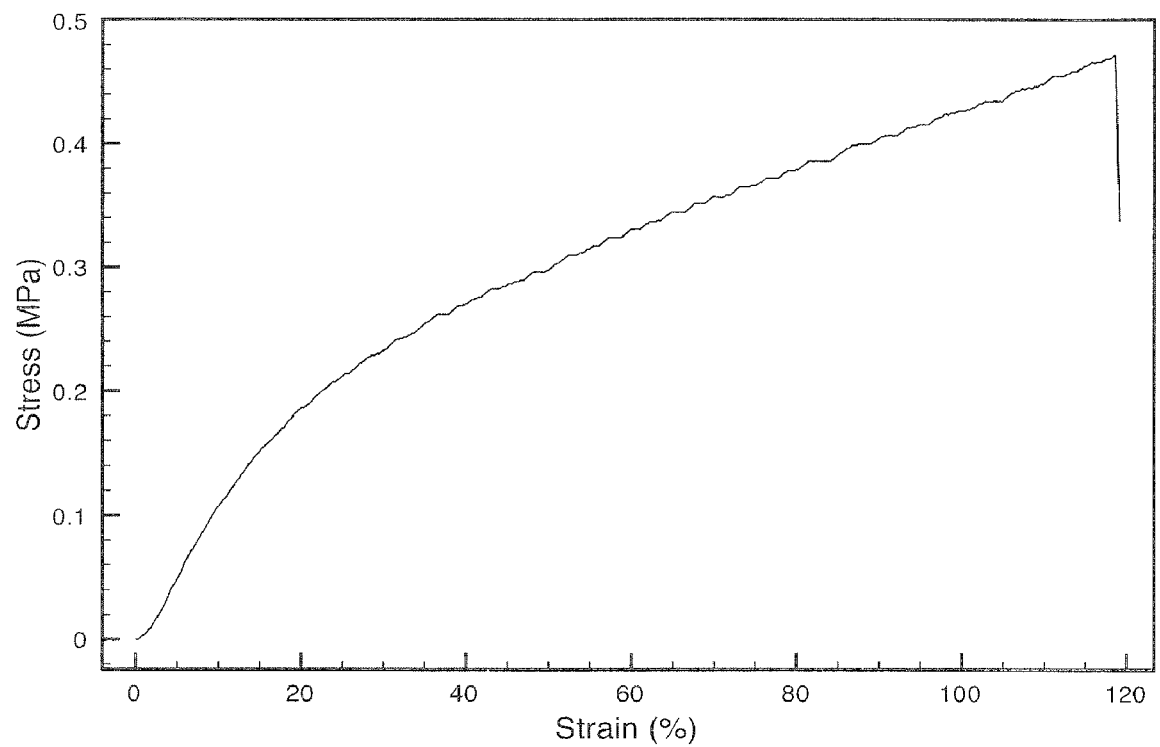
FIG. 3B is a graphical plot of the relationship between stress measured in MPa versus Strain measured as a percentage of the PGD elastomeric polymer at 37° C. illustrating a curve being representative of a non-linear elastomer in accordance with the compositions and methods of the present disclosure.

We found a statistically significant difference between specimens tested at 21° C. and 37° C. During extension at 21° C., PGD showed the typical linear elastic stress strain response followed by necking and plastic deformation of an elastic-plastic material, while at 37° C. PGD showed a non-linear elastomeric response (FIGS. 3A and 3B).

The tangent Young modulus dropped from a maximum of 136.55 (67.2-155.7) MPa to 1.08 (0.25-2.6) MPa at 21° C. and 37° C. respectively; tangent modulus at 37° C. was calculated at a strain level of 7.8% (5.5-9.8). Strain at break (SAB) at 21° C. was 225% (192.1-243.5) dropping to 123.2% (62.9-163.6) at 37° C.

The one-term Ogden constants were $\mu_1$=0.3±0.12 MPa, $\alpha_1$=2.14±0.5 with $R^2$=0.998±0.001 for the nonlinear elastic response at 37° C., demonstrating that PGD can be modeled using classic hyperelastic models.

Example 5

In-Vitro Degradation

Slabs of dry PGD (n=15) were weighted and placed in 15 ml conical test tubes (Falcon Bedford, Mass.) and allowed to soak in PBS (Gibco, Carlsbad, Calif.) at 37° C. for 20, 40 and 90 days. Samples were removed at the different time-points, dried at 40° C. and weighted again. Dry weight change was thus determined. A linear regression model was fit to the data obtained. Normalized change in dry weight was negligible in the first 20 days of soaking in PBS at 37° C., at 40 days. The weight dropped to 94.2% (93.1-95.3%), progressing to 87.4% (85.7-88.4%) at 90 days. Fitting a linear regression model to the data obtained we found the function y=−0.001x+1 where y is the ratio of residual biopolymer, −0.001 is the rate of degradation, x is the time in days and the coefficient 1 is the amount of polymer at time 0. This function predicted PGD in-vivo degradation behavior with a p-value less than 0.005%. and $R^2$ of 0.978. From this formula we calculated the time at which PGD would be 50% of its original weight (half-life) and found an estimated time of 16 months in physiological buffer and/or in situ within an animal subject.

Example 6

Biodegradability of the PGD Elastomeric Polymer

In-vitro degradation was assessed by soaking specimens (n=20) in PBS at 37° C. and measuring their dry weight after 20, 40, 60 and 90 days. Data were expressed as a median and range. ANOVA with Tukey HSD was used to compare means between groups (p<0.05). Degradation data was fit to a linear regression model to estimate the polymer halt-life.

A statistically significant difference was found between specimens tested at 25° and 37° C. Specimens at 25° C. exhibit classic linear elastic-plastic mechanical behavior while those at 37° C. exhibit nonlinear elastic behavior. Modulus and SAB are summarized in table 1. Stress-strain plots show a plastic and elastomeric behavior at 25 and 37° C. respectively. (FIGS. 3A and 3B) DSC confirmed a glass transition temperature of 32.1° C. (31-34.2° C.); no melting point was detected with TGA. PGD allowed cell growth with a confluence of 70-75% after a week in culture. In some embodiments, the estimated PGD half-life in PBS at 37° C. was approximately 16 months.

Example 7

Cell Growth and WST-1 Assay

To fabricate PGD-coated plates (PP), a solution of 1% PGD and tetrahydrofuran (THF) was casted on thirty-six 35 mm glass Petri dishes and after THF evaporation, the plates were cured with the same protocol described above. The culture plates were rinsed several times in 70% ethanol, sterile PBS to wash any unreacted monomer, and finally stored in PBS until their use. Human aortic fibroblasts (Promocell, Germany) (plating density=2000 cells/cm$^2$) were used as the cell type. Cell viability was studied over time by WST-1 cell proliferation assay (Roche, Basel, Switzerland). WST-1 cell proliferation assay was assessed by withdrawing plates (n=6) at 6 different time points. WST-1 reagent (200 µl) was added to each plate and incubated overnight. The drift in absorbance was detected at 480 nm with a plate reader (Genios plus, Tecan Ltd., Switzerland) driven by Magellan software (Tecan Ltd., Switzerland). Cells form each plate were counted with a hemocytometric slide. Cell number was calculated as density, by normalizing the number of cells per each plate to the area of the plates. For the control plates (CP), we plated the same cells with the same protocol onto thirty-six 35 mm un-coated polystyrene plates. A protocol identical to PGD plates was followed. The two groups were followed under microscopy to assess confluence.

Growth study showed that the density of human fibroblasts onto PP increases slower than controls at first, however the rate increases around day 10 in culture remaining constant until day 18, when the growth rate begins to slow down. CP, on the other hand, had a fast growth rate reaching confluence (microscopy) around day 10. At this time they showed a density peak that decreased slightly and maintained a plateau until the end of the study. PP reached the same density of the controls around day 18. At this time they also reached confluence (FIG. 4A) as also observed microscopically. WST-1 assay showed a pattern similar to the density curve, with a drop for CP starting at day 10, and for PP around day 18. (FIG. 4B)

Example 8

Shape Memory Assessment

To assess PGD shape memory properties, tensile test coupons (n=10) made according to the ASTM standard D 412-98a was used, and the same set-up used for mechanical testing. The initial gauge length ($L_0$) was stretched, at room temperature, to three different strain levels (60, 80, 100%). All the specimens were placed in a warm tap water bath at 40° C. Within 20 seconds specimens returned to their original size, the specimens were measured. The specimens were compared between the new lengths with each pre-stretch length. This cycle was repeated three times per each coupon.

PGD was also tested for shape memory after warm elongation. Briefly, tensile test coupons were elongated at 37° C. by using the same set-up used for the tensile tests described above, and employing 60, 80 and 100% strains. Once achieved the final configuration the coupons were cooled down to 21° C. to keep their deformed configuration. Finally, they were immersed in a warm bath at 40° C.; within 20 seconds, they returned to their original length that was measured. This cycle was repeated three times per each specimen. Our preliminary study demonstrated that PGD has distinct shape memory features.

Every specimen, elongated to the different strains levels (60, 80 and 100%), during cold draw or warm elongation, returned exactly to its original length ($L_0$) within 20 seconds after immersion in warm water, every single time this cycle was repeated. PGD showed: 1) a cold deformation temperature range (below 32° C.) and 2) a warm deformation temperature range (37° C. and above). During cold draw the polymer maintains the degree of deformation and shape we apply; during warm elongation the deformation is not maintained unless the polymer is cooled down rapidly. Regardless of the method for forming the deformed configuration (through cold or warm deformation) the PGD elastomeric polymer returns to its original shape when heated to 32° C. and above.

Statistics

We used SPSS statistical software (SPSS Inc. Chicago, Ill.). ANOVA with Tukey HSD was used to compare means between groups (p<0.05). Degradation data was fit to a linear regression model to estimate the polymer half-life.

Example 9

Manufacture of a Heart Valve and Treatment of A Heart Valve Defect

Heart valve tissue defects that benefit from replacement heart valves (mitral tricuspid, and aortic valves) can include congenital valve disorders, leaky valves that don't close properly (regurgitation), infected valves, and narrowed valves that don't open correctly (stenosis). For some heart valve tissue defects, a trileaflet heart valve medical device can be implanted to successfully treat the heart valve defect. A trileaflet heart valve includes an annular valve base with an inner surface forming an orifice through which blood flows from the upstream side to the downstream side. Three protruding hinges, each with concave sockets on opposite sides, are formed on the inner surface. Each hinge has a downstream face and an upstream face connected by a ridge. Three leaflets are respectively arranged between adjacent hinges. Each leaflet has round pivots on both sides that rest inside the concave sockets, allowing the leaflets to freely rotate in the annular valve base. When the leaflets are subject to a positive pressure from the blood flow, the leaflets are pushed open and allow a central flow. When the leaflets are subject to a negative pressure, the leaflets are closed to occlude the blood flow.

For complex tridimensional structures, a solid free form fabrication technology with indirect casting method can be used. The first stage of creating a 3D trileaflet valve was to realize a wax mold using a rapid prototyping technique (PatternMaster, Solidscape Inc. Merrimack, N.H.). (FIG. 5A). A polyurethane resin is then casted into the wax mold, (FIG. 5B) and left to cure for 24 h at room temperature. The polyurethane valve replica is then encased in polydimethylsiloxane (PDMS) (Dow Chemical Corporation, Midland, Mich.) which is left to cure for 24 h at room temperature or 1 h at 50° C. Once the PDMS mold has hardened, the polyurethane replica is removed (FIG. 5C) and the liquid PGD injected in it. Mold and PGD are placed in the vacuum oven for the curing process, to obtain the valve. (FIG. 5D).

The description of the present technology is merely exemplary in nature and, thus, variations that do not depart from the gist of the teachings are intended to be within the scope of the teachings. Such variations are not to be regarded as a departure from the spirit and scope of the teachings.

What is claimed is:

1. A biodegradable elastomeric polymer composition comprising, a cross-linked polyester having shape memory, said cross-linked polyester comprising a polymeric unit of monomers of glycerol and monomers of dodecanedioic acid, wherein the molar ratio of glycerol to dodecanedioic acid ranges from about 5:1 to about 1:5, wherein said elastomeric polymer composition exhibits stiff linear elastic/ductile plastic behavior by having a tensile Young's modulus ranging from about 67.2 to 155.7 megapascals (MPa) at 21° C. and exhibits compliant nonlinear elastic behavior with a tangent tensile Young's modulus ranging from about 0.25 MPa to about 2.6 MPa at 37° C. when measured according to American Society for Testing and Materials (ASTM) standard D412-98a.

2. The biodegradable elastomeric polymer composition according to claim 1, wherein the glass transition temperature ($T_g$) ranges from about 31° C. to about 35° C. when measured using differential scanning calorimetry.

3. The biodegradable elastomeric polymer composition according to claim 1, wherein the elastomeric polymer composition has a half life ranging from about 12 months to about 24 months when implanted in vivo or in physiological buffer.

4. The biodegradable elastomeric polymer composition according to claim 1, wherein the elastomeric polymer composition further comprises a plurality of porogens, said plurality of porogens being present in the elastomeric polymer composition in an amount ranging from about 50% to about 90% per volume of the total volume of the elastomeric polymer composition.

5. The biodegradable elastomeric polymer composition according to claim 1, wherein the elastomeric polymer composition comprises a porosity ranging from about 20% to about 90%.

6. The biodegradable elastomeric polymer composition according to claim 1, wherein the elastomeric polymer composition comprises at least one bioactive agent.

7. The biodegradable elastomeric polymer composition according to claim 1, further comprising a plurality of cells obtained from one or more of autogenic sources, allogeneic sources and xenogeneic sources, said plurality of cells being disposed on a surface of the elastomeric polymer composition.

8. The biodegradable elastomeric polymer composition according to claim 1, wherein the composition is in the form of a sheet, a membrane, a mesh, a sponge, a patch, a cylinder, a molded medical device or a combination thereof.

9. A method for forming a tissue engineered device, said method comprising the steps of:

providing a biodegradable elastomeric prepolymer composition, said elastomeric prepolymer composition comprising a polyester having repeating units of poly(glycerol dodecanoate);

placing said prepolymer composition in a device mold having a desired shape;

heating said device mold containing said prepolymer at a temperature ranging from about 70° C. to about 500° C. being maintained at a pressure ranging from 760 Torrs to about 50 milliTorrs thereby thermally curing said prepolymer composition and forming a molded poly(glycerol dodecanoate) device comprising the biodegradable elastomeric polymer composition of claim 1;

cooling said molded poly(glycerol dodecanoate) device; and removing said molded poly(glycerol dodecanoate) device from said device mold thereby forming a tissue engineered device.

10. The method according to claim 9, wherein said device mold is formed by: fabricating a wax mold using a rapid prototyping technique;

casting a polyurethane resin in said wax mold to form a polyurethane device replica;

covering said polyurethane device replica with a solution of polydimethylsiloxane;

curing said polydimethylsiloxane; and removing said polyurethane device replica from said polydimethylsiloxane to form the device mold.

11. The method according to claim 9, wherein said elastomeric prepolymer composition is in the form of a viscous solution.

12. A biodegradable elastomeric polymer composition comprising: a cross-linked polyester having shape memory, said cross-linked polyester comprising a polymeric unit of monomers of glycerol and monomers of dodecanedioic acid, wherein the elastomeric polymer has a cross-linking density of about $1.35 \times 10^{-4}$ mol/cm$^3$ when the molar ratio of glycerol:dodecanedioic acid is 1:1.

13. The biodegradable elastomeric polymer composition of claim 12, wherein the biodegradable elastomeric polymer composition has a porosity ranging from about 20% to about 90% by volume.

14. The biodegradable elastomeric polymer composition of claim 12, wherein the biodegradable elastomeric polymer composition further comprises a plurality of porogens present in the elastomeric polymer composition in an amount ranging from about 50% to about 90% per volume of the total volume of the elastomeric polymer composition.

* * * * *

UNITED STATES PATENT AND TRADEMARK OFFICE
CERTIFICATE OF CORRECTION

PATENT NO. : 8,236,350 B2
APPLICATION NO. : 12/533368
DATED : August 7, 2012
INVENTOR(S) : Francesco Migneco et al.

It is certified that error appears in the above-identified patent and that said Letters Patent is hereby corrected as shown below:

Title Page, No. (57), Abstract, line 6      "an PGD" should be --a PGD--.
(application page 56, line 6)

Title Page, No. (57), Abstract, line 10      "needs" should be --need--.
(application page 56, line 9)

Column 3, line 33      "O 31.54%" should be --O=31.54%--.
(application page 5, line 17)

Column 3, line 41      "O—H" should be --OH--.
(application page 5, line 17)

Column 4, line 1      After "MPa" delete ".".
(application page 6, line 7)

Column 4, line 29      "an $R^2$" should be --a $R^2$--.
(application page 6, line 29)

Column 5, line 7      "possess" should be --possesses--.
(application page 8, line 4)

Column 5, line 58      "temperatures" should be --temperature--.
(application page 9, line 12)

Column 6, line 18      After first occurrence of "the" delete "a".
(application page 10, line 4)

Column 6, line 28      After "170%" delete ";" and insert --.--.
(application page 10, line 12)

Signed and Sealed this
Fourth Day of December, 2012

David J. Kappos
*Director of the United States Patent and Trademark Office*

CERTIFICATE OF CORRECTION (continued)

U.S. Pat. No. 8,236,350 B2

| | |
|---|---|
| Column 10, line 33 (application page 17, line 24) | "UGA" should be --L/GA--. |
| Column 12, line 30 (application page 21, line 7) | "ingibitors" should be --inhibitors--. |
| Column 16, line 17 (application page 27, line 20) | After "environments" insert --.--. |
| Column 16, line 24 (application page 27, lines 25-26) | "or and" should be --and/or--. |
| Column 17, line 23 (application page 29, line 15) | After "regeneration" insert --.--. |
| Column 17, line 65 (application page 30, line 18) | After "defects" delete ".". |
| Column 19, line 1 (application page 32, line 12) | After "then" insert --be--. |
| Column 19, lines 18-19 (application page 32, line 25) | "platelets etc)" should be --platelets, etc.)--. |
| Column 20, line 42 (application page 35, line 4) | After "early" delete "in the". |
| Column 21, line 50 (application page 37, line 1) | "FIG. 5A-5D" should be --FIGS. 5A-5D--. |
| Column 24, line 36 (application page 41, line 27) | After "articles" insert --.--. |
| Column 25, line 51 (application page 43, line 28) | After "16 months" insert --.--. |
| Column 26, line 24 (application page 45, line 4) | "O 31.54%" should be --O=31.54%--. |
| Column 26, line 29 (application page 45, line 7) | "$0.2 \times 10^{4}$" should be --$0.2 \times 10^{-4}$--. |
| Column 26, line 49 (application page 45, line 18) | After "(n=20)" insert --.--. |

CERTIFICATE OF CORRECTION (continued)
U.S. Pat. No. 8,236,350 B2

| | |
|---|---|
| Column 26, line 60 (application page 45, line 26) | "O-H" should be --OH--. |
| Column 27, line 32 (application page 46, line 22) | "$\mu_i$ and $\alpha_i$" should be --$\mu_1$ and $\alpha_1$--. |
| Column 27, line 61 (application page 47, line 14) | After "fit" insert --.--. |
| Column 28, line 38 (application page 48, line 16) | After "0.005%" delete ".". |
| Column 28, line 55 (application page 48, line 25) | "halt-life" should be --half-life--. |
| Column 29, line 21 (application page 49, line 18) | "form" should be --from--. |